United States Patent
Nirogi et al.

(10) Patent No.: US 8,653,071 B2
(45) Date of Patent: Feb. 18, 2014

(54) $\alpha_4\beta_2$ NEURONAL NICOTINIC ACETYLCHOLINE RECEPTOR LIGANDS

(75) Inventors: Ramakrishna Nirogi, Hyderabad (IN); Abdul Rasheed Mohammed, Hyderabad (IN); Kana Ram Kumawat, Hyderabad (IN); Ishtiyaque Ahmad, Hyderabad (IN); Pradeep Jayarajan, Hyderabad (IN); Anil Karbhari Shinde, Hyderabad (IN); Nagaraj Vishwottam Kandikere, Hyderabad (IN); Koteshwara Mudigonda, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 13/519,298

(22) PCT Filed: May 3, 2010

(86) PCT No.: PCT/IN2010/000285
§ 371 (c)(1),
(2), (4) Date: Aug. 20, 2012

(87) PCT Pub. No.: WO2011/080751
PCT Pub. Date: Jul. 7, 2011

(65) Prior Publication Data
US 2012/0322808 A1 Dec. 20, 2012

(30) Foreign Application Priority Data
Dec. 29, 2009 (IN) .......................... 3195/CHE/2009

(51) Int. Cl.
*A61K 31/5377* (2006.01)
*A61K 31/497* (2006.01)
*A61K 31/496* (2006.01)
*A61K 31/4709* (2006.01)
*A61K 31/4427* (2006.01)
*A61K 31/404* (2006.01)
*A61K 31/403* (2006.01)
*C07D 413/14* (2006.01)
*C07D 401/02* (2006.01)
*C07D 401/14* (2006.01)
*C07D 215/00* (2006.01)
*C07D 209/04* (2006.01)
*C07D 209/02* (2006.01)

(52) U.S. Cl.
USPC ............. 514/235.2; 514/253.09; 514/255.05; 514/311; 514/339; 514/410; 514/414; 514/415; 544/124; 544/364; 544/405; 546/152; 546/276.7; 548/452; 548/455; 548/465

(58) Field of Classification Search
USPC ........... 514/235.2, 253.09, 255.05, 311, 339, 514/410, 414, 415; 544/124, 364, 405; 546/152, 276.7; 548/452, 455, 465
See application file for complete search history.

(56) References Cited

U.S. PATENT DOCUMENTS

2004/0192673 A1   9/2004  Gaillard et al.

FOREIGN PATENT DOCUMENTS

| EP | 0296560 B1 | 2/1996 |
| EP | 1386920 A1 | 2/2004 |
| WO | 0196302 A1 | 12/2001 |
| WO | 2004041816 A1 | 5/2004 |
| WO | 2008057938 A1 | 5/2008 |
| WO | 2008081399 A2 | 7/2008 |
| WO | 2009016564 A2 | 2/2009 |

OTHER PUBLICATIONS

Monteggia, Lisa M. et al, "Cloning and Transient Expression of Genes Encoding the Human Alpha4 and Beta2 Neuronal Nicotinic Acetylcholine Receptor (nAChR) Subunits", Gene, Elsevier Science B.V., USA, vol. 155, 1995, pp. 189-193.

Graham, A., et al, "Immunohistochemical Localisation of Nicotinic Acetylcholine Receptor Subunits in Human Cerebellum", Neuroscience, Pergamon, GB, vol. 113, No. 3, 2002, pp. 493-507.

Hogg, R.C., et al, "Nicotinic Acetylcholine Receptors: From Structure to Brain Function", Rev Phhysiol Biochem Pharmacol, ONLINE Springer-Verlag, vol. 147, 2003, pp. 1-46.

Hogg, R.C. and Bertrand, D., "Nicotinic Acetylcholine Receptors as Drug Targets", Current Drug Targets, Bentham Science Publishers Ltd., vol. 3, 2004, pp. 123-130.

Suto, Mark J. and Zacharias, Niki, "Neuronal Nicotinic Acetylcholine Receptors as Drug Targets", Expert Opin. Ther: Targets, Ashley Publications Ltd, vol. 8, No. 2, 2004, pp. 61-64.

(Continued)

Primary Examiner — Samantha Shterengarts
(74) Attorney, Agent, or Firm — IPHorgan, Ltd.

(57) ABSTRACT

The present invention relates to novel $\alpha_4\beta_2$ neuronal nicotinic acetylcholine receptor ligand compounds of the formula (I), and their derivatives, stereoisomers, pharmaceutically acceptable salts and compositions containing them. The present invention relates to novel α4β2 neuronal nicotinic acetylcholine receptor ligand compounds of the formula (I), and their derivatives, stereoisomers, pharmaceutically acceptable salts and compositions containing them.

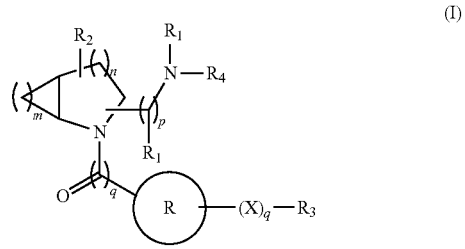

9 Claims, No Drawings

(56) References Cited

OTHER PUBLICATIONS

Newhouse, Paul A., et al., "Effects of Nicotinic Stimulation on Cognitive Performance", Current Opinion in Pharmacology, Science Direct, vol. 4, 2004, pp. 36-46.

Levin, E.D. and Rezvani, A.H., "Nicotinic Treatment for Cognitive Dysfunction", Current Drug Targets, Bentham Science Publishers Ltd., vol. 1, 2002, pp. 423-431.

Graham, A.J. et al, "Human Brain Nicotinic Receptors, their Distribution and Participation in Neuropsychiatric Disorders", Current Drug Targets, Bentham Science Publishers Ltd., vol. 1, 2002, pp. 387-397.

Mcevoy, Joseph P. and Allen, Trina B., "The Importance of Nicotinic Acetylcholine Receptors in Schizophrenia, Bipolar Disorder and Tourette's Syndrome", Current Drug Targets, Bentham Science Publishers Ltd., vol. 1, 2002, pp. 433-442.

Vincler, Michelle, "Neuronal Nicotinic Acetylcholine Receptors as Targets for Novel Analgesics", Expert Opin. Investig. Drugs, Ashley Publications Ltd, vol. 14, No. 10, 2005, pp. 1191-1198.

Decker, Michael W. et al, "The Therapeutic Potential of Nicotinic Acetylcholine Receptor Agonists for Pain Control", Expert Opin. Investig. Drugs, Ashley Publications Ltd, vol. 10, No. 10, 2001, pp. 1819-1830.

Miao, F. J.-P. et al, "Central Terminals of Nociceptors are Targets for Nicotine Suppression of Inflammation", Neuroscience, Elsevier Ltd., vol. 123, 2004, pp. 777-784.

Shytle, R. Douglas, Ph.D. et al, "Neuronal Nicotinic Receptor Inhibition for Treating Mood Disorderse: Preliminary Controlled Evidence with Mecamylamine", Depression and Anxiety, Wiley InterScience, vol. 16, 2002, pp. 89-92.

O'Neill, M.J. et al, "The Role of Neuronal Nicotinic Acetylcholine Receptors in Acute and Chronic Neurodegeneration", Current Drug Targets, Bentham Science Publishers Ltd., vol. 1, 2002, pp. 399-411.

Dwoskin, Linda P. and Crooks, Peter A., "A Novel Mechanism of Action and Potential Use for Lobeline as a Treatment for Psychostimulant Abuse", Biochemical Pharmacology, Elsevier Science Inc., vol. 63, 2002, pp. 89-98.

Coe, Jotham W. et al, "3,5-Bicyclic aryl piperidines: A novel class of Alpha4Beta2 Neuronal Nicotinic Receptor Partial Agonists for Smoking Cessation", Bioorganic & Medicinal Chemistry Letters, Elsevier Ltd, vol. 15, 2005, pp. 4889-4897.

Li, Ming D. et al, "Nicotine, Body Weight and Potential Implications in the Treatment of Obesity", Current Topics in Medicinal Chemistry, vol. 3, 2003, pp. 899-919.

Shytle, RD et al, "Nicotinic Acetylcholine Receptors as Targets for Antidepressants", Molecular Psychiatry, Nature Publishing Group, vol. 7, 2002, pp. 525-535.

Jiaqiang Cai et al; "Antagonists of the Orexin Receptors", Expert Opinion on Therapeutic Patents, Informa Healthcare, GB, vol. 16, No. 5, May 1, 2006, pp. 631-646.

European Patent Office, International Search Report, International Search Authority, PCT International Patent Application No. PCT/IN2010/000285, Jun. 29, 2011.

$\alpha_4\beta_2$ NEURONAL NICOTINIC ACETYLCHOLINE RECEPTOR LIGANDS

FIELD OF INVENTION

The present invention relates to novel $\alpha_4\beta_2$ neuronal nicotinic acetylcholine receptor ligand compounds of the formula (I), and their derivatives, stereoisomers, pharmaceutically acceptable salts and compositions containing them.

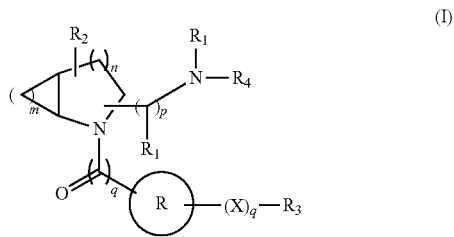

The present invention also relates to a process for the preparation of above said novel compounds, and their derivatives, stereoisomers and pharmaceutically acceptable salts.

The compounds of general formula (I) are useful in the treatment of various disorders that are related to $\alpha_4\beta_2$ nicotinic receptors.

BACKGROUND OF THE INVENTION

Nicotinic acetylcholine receptors (nAChRs) or Neuronal nicotinic receptors (NNRs) mediate a very wide range of physiological effects and have been targeted for therapeutic treatment of various disorders. nAChRs belonging to the super family of ligand gated ion channels (LGIC), are widely distributed throughout the central nervous system (CNS) and the peripheral nervous system (PNS). The NNRs are understood to play an important role in regulating CNS function and the release of many neurotransmitters. Typically, NNRs are constructed from a pentameric assembly of subunit proteins. Seventeen subunits of nAChRs have been identified to date, which are identified as $\alpha2$-$\alpha18$, $\beta1$-$\beta4$, $\gamma$, $\delta$, and $\epsilon$. Of these subunits, eight neuronal $\alpha$ ($\alpha2$ through $\alpha9$) and three neuronal $\beta$ ($\beta2$ through ($\beta4$), prominently exist in the mammalian brain. (See for examples, Monteggia L M et al., Cloning and transient expression of genes encoding the human alpha4 and beta2 neuronal nicotinic acetylcholine receptor (nAChR) subunits, Gene: 1995, 155:189-193; Graham A et al., Immunohistochemical localization of nicotinic acetylcholine receptor subunits in human cerebellum, Neuroscience. 2002; 113:493-507). Multiple functionally distinct nAChR complexes also exist; as a homomeric functional pentamer or combinations of different subunits can complex together (see for examples, Hogg, R. C et al., Nicotinic acetylcholine receptors: from structure to brain function, Rev. Physiol, Biochem. Pharmacol, 2003, 147: 1-46).

The identification of a family of genes coding for the nAChRs and increased knowledge of their expression and function in the central nervous system have lead to the increasing attention concerning their potential as drug targets. (See examples, Hogg R. C et al., Nicotinic Acetylcholine Receptors as Drug Targets, Curr. Drug Targets: CNS Neurol. Disord. 2004, 3: 123-130; Suto et al., Neuronal nicotinic acetylcholine receptors as drug targets, Expert Opin. Ther. Targets 2004, 8: 61-64).

There are many potential therapeutic uses for neuronal nicotinic $\alpha_4\beta_2$ receptor ligands in humans based on direct effects and on indications from available scientific studies. Neuronal nicotinic $\alpha_4\beta_2$ receptors have been implicated in different therapies like cognitive disorders, including Alzheimer's disease, Parkinson's disease, Attention deficit/hyperactivity disorder, Schizophrenia and Tourette's syndrome (See examples, Newhouse et al., Effects of nicotinic stimulation on cognitive performance, Curr. Opin. Pharmacol. 2004, 4: 36-46; Levin E. D et al., Nicotinic Treatment for Cognitive Dysfunction, Curr. Drug Targets: CNS Neurol. Disord. 2002, 1: 423-431; Graham A. J. et al., Human Brain Nicotinic Receptors, their Distribution and Participation in Neuropsychiatric Disorders, Curr. Drug Targets: CNS Neurol. Disord. 2002, 1: 387-397; McEvoy J. P et al., The Importance of Nicotinic Acetylcholine Receptors in Schizophrenia, Bipolar Disorder and Tourette's Syndrome, Curr. Drug Targets: CNS Neurol. Disord. 2002, 1: 433-442).

Studies in a variety of rodent pain models have demonstrated that $\alpha_4\beta_2$ receptor ligands have the potential for highly efficacious treatments in a variety of pain states and inflammation. (See examples, Vincler et al., Neuronal nicotinic receptors as targets for novel analgesics, Expert Opin. Invest. Drugs, 2005, 14: 1191-1198; Decker M W et al., The therapeutic potential of nicotinic acetylcholine receptor agonists for pain control, Expert Opin Investig Drugs. 2001 October; 10(10):1819-30; Miao et al., Central terminals of nociceptors are targets for nicotine suppression of inflammation, Neuroscience 2004, 123: 777-84).

Significant efforts are being made to understand the hypercholinergic neurotransmission, which is associated with depressed mood states suggesting that it may be mediated through excessive neuronal nicotinic receptor activation and that the therapeutic actions of many antidepressants may be, in part, mediated through inhibition of these receptors. Thus the neuronal nicotinic $\alpha_4\beta_2$ receptor ligands may represent a novel class of therapeutic agents for treating depression and anxiety disorders (See examples, Shytle et al., Nicotinic acetylcholine receptors as targets for antidepressants, Mol. Psychiatry 2002, 7: 525-35; Shytle et al., Neuronal nicotinic receptor inhibition for treating mood disorders: preliminary controlled evidence with mecamylamine, Depress. Anxiety, 2002, 16: 89-92). Recent studies have also been reported that the nAChRs play a role in neurodegenerative disorders. The nicotine and subtype selective nAChR ligands can provide neuroprotection in in-vitro cell culture systems and in in-vivo studies in animal models of such disorders. (See examples, O'Neill et al., The role of neuronal nicotinic acetylcholine receptors in acute and chronic neurodegeneration, Curr. Drug Targets: CNS Neurol. Disord. 2002, 1: 399-411).

The $\alpha_4\beta_2$ nAChR subtype has the highest affinity for nicotine and is the primary candidate for mediating nicotine's central effects. Chronic nicotine exposure (in humans, animals and cell culture systems) leads to an increase in the number of $\alpha_4\beta_2$ nAChR (upregulation), with functional implications for withdrawal. These studies suggested that the neuronal nicotinic $\alpha_4\beta_2$ receptor ligands play a critical role in the treatment of addiction. (Dwoskin et al., A novel mechanism of action and potential use for lobeline as a treatment for psychostimulant abuse, Biochem. Pharmacol. 2002, 63: 89-98; Coe et al., 3,5-Bicyclic aryl piperidines: a novel class of $\alpha_4\beta_2$ nAChR partial agonists for smoking cessation, Bioorg. Med. Chem. Lett. 2005, 15: 4889-97). The $\alpha_4\beta_2$ receptor ligands are also expected to be of use in the treatment of obesity (Li et al., Nicotine, body weight and potential implications in the treatment of obesity, Curr. Top. Med. Chem. 2003, 3: 899-919).

Taken together, the above studies strongly suggest that compounds which are $\alpha_4\beta_2$ receptor modulators, i.e. ligands, may be useful for therapeutic indications including, the treatment of diseases associated with a deficit in memory, cognition and learning such as Alzheimer's and attention deficit disorder; the treatment of personality disorders such as schizophrenia; the treatment of behavioral disorders, e.g. anxiety, depression and obsessive compulsive disorders; the treatment of pain and inflammation; the treatment of motion or motor disorders such as Parkinson's disease and epilepsy; the treatment of diseases associated with neurodegeneration such as stroke or head trauma or withdrawal from drug addiction including addiction to nicotine, alcohol and other substances of abuse and obesity.

Patent publications WO2008057938 (A1), US20040192673 (A1) & EP296560 (B1) disclosed series of compounds as ligands of nicotinic acetylcholine receptors and are claimed to be useful in the treatment of various CNS disorders. While some nicotinic acetylcholine receptor compounds have been disclosed, there continues to be a need for compounds that are useful for modulating nicotinic acetylcholine receptors. In our research in area of nicotinic acetylcholine receptors, we found that bicyclic compounds of formula (I) demonstrate very high nicotinic acetylcholine receptor affinity. Therefore, it is an object of this invention to provide compounds, which are useful as therapeutic agents in the treatment/prevention of a variety of central nervous system disorders or disorders affected by the $\alpha_4\beta_2$ nicotinic receptors.

SUMMARY OF THE INVENTION

The present invention relates to novel $\alpha_4\beta_2$ neuronal nicotinic acetylcholine receptor ligand compounds of the formula (I), and their derivatives, stereoisomers, pharmaceutically acceptable salts and compositions containing them.

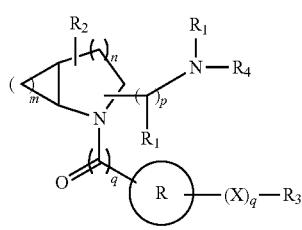

(I)

wherein

represents heteroaryl;

$R_1$ represents hydrogen or alkyl;

$R_2$ represents hydrogen or alkyl;

$R_3$ represents hydrogen, hydroxy, halogen, oxo, nitro, acyl, amide, amine, cyano, alkyl, alkoxy, cycloalkyl, cycloalkylalky, cycloalkoxy, haloalkyl, haloalkoxy, aryl, heteroaryl, heterocyclyl or heterocyclylalkyl;

$R_4$ represents hydrogen, alkyl, cycloalkyl, cycloalklyalkyl, aryl, heteroaryl, heterocyclyl or heterocyclylalkyl; optionally $R_1$ and $R_4$ along with nitrogen atom may form heteroaryl or heterocyclyl;

"X" represents C, N, O, S;

"m" represents 1 to 4;

"n" represents 1 to 2;

"p" represents 0 to 3;

"q" represents 0 to 1.

The present invention relates to use of a therapeutically effective amount of compound of formula (I), to manufacture a medicament in the treatment of various disorders that are related to $\alpha_4\beta_2$ nicotinic receptors.

Specifically, the compounds of this invention are useful in the treatment of various disorders such as anxiety, alzheimer's disease, depression, convulsive disorders, cognitive memory disorders, ADHD (Attention Deficient Disorder/Hyperactivity Syndrome), pain, psychosis, psychotic depression, parkinson's disease, schizophrenia, sleep disorders, withdrawal from drug abuse syndrome, mild cognitive impairment and obesity.

In another aspect, the invention relates to pharmaceutical compositions containing a therapeutically effective amount of at least one compound of formula (I), and their derivatives, stereoisomers and pharmaceutically acceptable salts thereof, in admixture with at least one suitable carrier, diluents, adjuvants or excipients.

In another aspect, the invention also provides a radiolabeled compound of formula (I) for use in medical diagnosis or therapy, as well as the use of a radiolabeled compound of formula (I) to prepare a medicament useful in the treatment of various disorders that are related to $\alpha_4\beta_2$ nicotinic receptors.

In another aspect, the invention relates to the use of a compound according to the present invention in combination with at least one further active ingredient for manufacture of a medicament for the treatment or prevention of diseases and conditions.

In still another aspect, the invention relates to compositions comprising and methods for using compounds of formula (I).

In yet another aspect, the invention further relates to the process for preparing compounds of formula (I) and their derivatives, stereoisomers and pharmaceutically acceptable salts.

Representative compounds of the present invention include those specified below and their derivatives, stereoisomers and pharmaceutically acceptable salts. The present invention should not be construed to be limited to them.

N-[2-(5-Bromopyridin-3-yl)-2-azabicyclo[3.1.0]hex-3-ylmethyl]-dimethylamine hydrochloride;

[2-(5-Bromopyridin-3-yl)-2-azabicyclo-[3.1.0]-hex-3-yl]methylamine;

Furan-2-yl-(3-methylaminomethyl-2-aza bicyclo[3.1.0]hex-2-yl)methanone tartarate;

N-[2-(Pyridin-3-yl)-2-azabicyclo[3.1.0]hex-3-ylmethyl]methylamine hydrochloride;

N-[2-(5-Bromopyridin-3-yl)-2-azabicyclo[3.1.0]hex-3-ylmethyl]ethylamine tartarate;

2-(5-Bromopyridin-3-yl)-3-pyrrolidin-1-ylmethyl-2-azabicyclo[3.1.0]hexane tartarate;

2-(5-Bromopyridin-3-yl)-3-(morpholin-4-ylmethyl)-2-azabicyclo[3.1.0]hexane tartarate;

2-(5-Bromopyridin-3-yl)-3-(piperazin-1-ylmethyl)-2-azabicyclo[3.1.0]hexane;

N-[2-(Pyridin-3-yl)-2-azabicyclo[3.1.0]hex-3-ylmethyl] dimethylamine;

N-[2-(5-Bromopyridin-3-yl)-2-azabicyclo[3.1.0]hex-3-ylmethyl]methylamine;

N-[2-(5-Chloropyridin-3-yl)-2-azabicyclo[3.1.0]hex-3-ylmethyl]methylamine fumarate;

[2-(5-Chloropyridin-3-yl)-2-aza-bicyclo[3.1.0]hex-3-yl]methylamine fumarate;

N-[2-(5-Methoxypyridin-3-yl)-2-azabicyclo[3.1.0]hex-3-yl-methyl]methylamine fumarate;
N-[2-(5-Isopropoxypyridin-3-yl)-2-azabicyclo[3.1.0]hex-3-ylmethyl]methylamine;
[2-(5-Phenylsulfanylpyridin-3-yl)-2-azabicyclo[3.1.0]hex-3-yl]methylamine fumarate;
N-[2-(5-phenylsulfanylpyridin-3-yl)-2-azabicyclo[3.1.0]hex-3-yl methyl]methylamine fumarate;
[2-(Pyridin-3-yl)-2-azabicyclo[3.1.0]hex-3-yl]methylamine fumarate;
[2-(3-Bromo-2-ethoxypyridin-5-yl)-2-azabicyclo[3.1.0]hex-3-yl-methyl]methylamine fumarate;
N-[2-(3-Hydroxy pyrazin-2-yl)-2-azabicyclo[3.1.0]hex-3-yl methyl]methylamine;
N-(2-(pyrimidin-5-yl)-2-azabicyclo[3.1.0]hex-3-ylmethyl) methyl amine fumarate;
N-(2-(2-trifluoromethylpyridin-5-yl)-2-azabicyclo[3.1.0]hex-3-ylmethyl)methyl amine fumarate;
N-(2-(2-trifluoromethylpyridin-5-yl)-2-azabicyclo[3.1.0]hex-3-ylmethyl)amine fumarate;
N-(2-(2-chloro pyridin-5-yl)-2-azabicyclo[3.1.0]hex-3-ylmethyl)amine fumarate;
N-(2-(3-methylpyridin-5-yl)-2-azabicyclo[3.1.0]hex-3-ylmethyl)amine fumarate;
N-(2-(3-methylpyridin-5-yl)-2-azabicyclo[3.1.0]hex-3-ylmethyl)methyl amine bistartarate;
N-(2-(3-trifluoromethylpyridin-5-yl)-2-azabicyclo[3.1.0]hex-3-ylmethyl)amine fumarate;
N-(2-(quinolin-3-yl)-2-azabicyclo[3.1.0]hex-3-ylmethyl) amine fumarate;
N-(2-(3-trifluoromethylpyridin-5-yl)-2-azabicyclo[3.1.0]hex-3-ylmethyl)methylamine fumarate;
N-(2-(quinolin-3-yl)-2-azabicyclo[3.1.0]hex-3-ylmethyl) methylamine fumarate;
Benzofuran-2-yl-(3-methylaminomethyl-2-azabicyclo[3.1.0]hex-2-yl)methanone tartrate;
(7-Bromo benzofuran-2-yl)-(3-methylaminomethyl-2-azabicyclo[3.1.0]hex-2-yl)methanone tartrate;
(3-Aminomethyl-2-azabicyclo[3.1.0]hex-2-yl)-(1H-indol-2-yl)-methanone;
(3-Aminomethyl-2-aza bicyclo[3.1.0]hex-2-yl)furan-2-yl methanone tartrate;
(3-Aminomethyl-2-azabicyclo[3.1.0]hex-2-yl)(5-bromo pyridin-3-yl)methanone tartrate;
(3-Aminomethyl-2-azabicyclo[3.1.0]hex-2-yl)pyridin-2-yl methanone tartrate;
(3-Aminomethyl-2-aza bicyclo[3.1.0]hex-2-yl)pyridin-3-yl methanone tartarate;
(3-Aminomethyl-2-aza-bicyclo[3.1.0]hex-2-yl)pyridin-4-yl methanone tartarate;
N-[2-(pyridin-3-yl)-2-azabicyclo[3.1.0]hex-3-ylmethyl)methylamine;
5-(3-Methylaminomethyl-2-azabicyclo[3.1.0]hex-2-yl) nicotinonitrile;
N-[2-(2,3-Dichloropyridin-5-yl)-2-azabicyclo[3.1.0]hex-3-ylmethyl]methylamine;
N-[2-(5-Isopropoxypyridin-3-yl)-2-azabicyclo[3.1.0]hex-3-ylmethyl]methylamine;
N-[2-(5-methylpyridin-3-yl)-2-azabicyclo[3.1.0]hex-3-ylm-ethyl]methylamine;
1-[5-(3-Methylaminomethyl-2-azabicyclo[3.1.0]hex-2-yl)pyridin-3-yl]pyrrolidin-2-one;
5-(3-Methylaminomethyl-2-azabicyclo[3.1.0]hex-2-yl) nicotinamide;
N-[2-(5-Bromopyridin-3-yl)-2-azabicyclo[3.1.0]hex-3-ylm-ethyl]methylamine;
N-[2-(5-Methoxypyridin-3-yl)-2-azabicyclo[3.1.0]hex-3-yl-methyl]methylamine;
[5-(3-methylaminomethyl-2-azabicyclo[3.1.0]hex-2-yl)pyridin-3-yl]methylamine;
2-(5-Bromopyridin-3-yl)-3-(pyrrolidin-1-ylmethyl)-2-azabicyclo[3.1.0]hexane;
[2-(5-Bromopyridin-3-yl)-2-azabicyclo[3.1.0]hex-3-yl]me-thylamine;
N-[2-(pyridin-3-yl)-2-azabicyclo[3.1.0]hex-3-ylmethyl) dimethylamine;
5-(3-Dimethylaminomethyl-2-azabicyclo[3.1.0]hex-2-yl) nicotinonitrile;
N-[2-(2,3-Dichloropyridin-5-yl)-2-azabicyclo[3.1.0]hex-3-ylmethyl]dimethylamine;
N-[2-(5-Isopropoxypyridin-3-yl)-2-azabicyclo[3.1.0]hex-3-ylmethyl]dimethylamine;
N-[2-(5-methylpyridin-3-A-2-azabicyclo[3.1.0]hex-3-ylm-ethyl]dimethylamine;
1-[5-(3-Dimethylaminomethyl-2-azabicyclo[3.1.0]hex-2-yl)pyridin-3-yl]pyrrolidin-2-one;
5-(3-Dimethylaminomethyl-2-azabicyclo[3.1.0]hex-2-yl) nicotinamide;
[2-(5-Bromopyridin-3-yl)-2-azabicyclo[3.1.0]hex-3-ylm-ethyl]dimethylamine;
N-[2-(5-Methoxypyridin-3-yl)-2-azabicyclo[3.1.0]hex-3-yl-methyl]dimethylamine;
[5-(3-Dimethylaminomethyl-2-azabicyclo[3.1.0]hex-2-yl) pyridin-3-yl]methylamine;
(3-Aminomethyl-2-azabicyclo[3.1.0]hex-2-yl)-benzofuran-2-yl-methanone;
(3-Aminomethyl-2-azabicyclo[3.1.0]hex-2-yl)-(7-bromobenzofuran-2-yl)methanone;
(4-Chloro furan-2-yl)(3-methylaminomethyl-2-azabicyclo[3.1.0]hex-2-yl)methanone;
(3-Aminomethyl-2-azabicyclo[3.1.0]hex-2-yl)-(4-bromo furan-2-ylmethanone;
(3-Aminomethyl-2-azabicyclo[3.1.0]hex-2-yl)-(4-chloro-furan-2-yl)methanone and
(4-Chlorofuran-2-yl)-(3-methylaminomethyl-2-azabicyclo[3.1.0]hex-2-yl)methanone.

DETAILED DESCRIPTION OF THE INVENTION

Unless otherwise stated, the following terms used in the specification and claims have the meanings given below:

The term "halogen" means fluorine, chlorine, bromine or iodine.

The term "alkyl" means straight chain or branched hydrocarbon radical consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.

The term "alkoxy" means an alkyl group attached via an oxygen linkage to the rest of the molecule. Exemplary "alkoxy" groups include methoxy, ethoxy, propyloxy, iso-propyloxy and the like.

The term "cycloalkyl" means non-aromatic mono or multi cyclic ring systems of 3 to 12 carbon atoms. Exemplary "cycloalkyl" groups include cyclopropyl, cyclobutyl, cyclopentyl and the like.

The term "cycloalkylalkyl" means cycloalkyl group directly attached to alkyl group.

The term "cycloalkoxy" means non-aromatic mono or multi cyclic ring systems of 3 to 12 carbon atoms. Exemplary "cycloalkoxy" groups include cyclopropyloxy, cyclobutyloxy, cyclopentyloxy, cyclohexyloxy and the like.

The term "haloalkyl" means straight or branched chain alkyl radicals containing one to three carbon atoms. Exemplary "haloalkyl" groups include fluoromethyl, difluoromethyl, trifluoromethyl, trifluoroethyl, fluoroethyl, difluoroethyl and the like.

The term "haloalkoxy" means straight or branched chain alkoxy radicals containing one to three carbon atoms. Exemplary "haloalkoxy" groups include fluoromethoxy, difluoromethoxy, trifluoromethoxy, trifluoroethoxy, fluoroethoxy, difluoroethoxy and the like.

The term "aryl" means any functional group or substituent derived from a simple aromatic ring, Exemplary "aryl" groups include phenyl, naphthyl and the like.

The term "heteroaryl" means organic compounds that contain a ring structure containing atoms in addition to carbon such as sulfur, oxygen or nitrogen, as part of the ring, these additional atoms may be repeated more than once in ring. These rings may be either simple aromatic rings or non-aromatic rings. Exemplary "heteroaryl" groups include pyridine, pyrimidine, benzofuranyl, benzothiophene, furyl, dioxalanyl, pyrrolyl, oxazolyl, pyridyl, pyridazinyl, pyrimidinyl, pyrazinyl, quinolinyl, indolyl and the like.

The term "heteroaralkyl" means heteroaryl ring radical directly bonded to an alkyl group.

The term "heterocyclyl" means 3 to 12-membered rings, whose ring structures include 1 to 3 heteroatoms, these additional atoms may be repeated more than once in ring. Exemplary "heterocyclyl" groups include pyrrolidinyl, piperidinyl, piperazinyl, morpholinyl and the like.

The term "heterocyclylalkyl" means heterocyclyl ring directly attached to alkyl group.

The following groups may be substituted or unsubstituted, they are cycloalkyl, cycloalkylalkyl, cycloalkoxy, aryl, heteroaryl, heteroaralkyl, heterocyclyl and heterocyclylalkyl. Optionally substituents on these groups may be selected from the group consisting of hydrogen, hydroxy, halogen, nitro, thio, oxo, carboxylic, amine, amide, alkyl, alkoxy, haloalkyl or haloalkoxy.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers). It also includes rotamers, which are conformers that differ by rotation about only one single σ bond.

The term "derivative" refers to a compound obtained from a compound according to formula (I), and their stereoisomers and pharmaceutically acceptable salts thereof, by a simple chemical process converting one or more functional groups such as by oxidation, hydrogenation, alkylation, esterification, halogenation and the like.

The terms "treating", "treat" or "treatment" embrace all the meanings such as preventative, prophylactic and palliative.

The phrase "pharmaceutically acceptable salts" indicates that the substance or composition must be compatible chemically and/or toxicologically, with the other ingredients comprising a formulation, the mammal being treated therewith.

The phrase "Therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition or disorder described herein.

Commercial reagents were utilized without further purification. Room temperature refers to 25-30° C. IR were taken using KBr and in solid state. Unless otherwise stated, all mass spectra were carried out using ESI conditions. $^1$H-NMR spectra were recorded at 400 MHz on a Bruker instrument. Deuterated chloroform (99.8% D) was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

The compounds of the invention can be used in combination with other therapeutic agents or approaches used to treat or prevent the conditions listed above. Such agents or approaches include 5-HT$_{1-7}$ receptors, GABA inverse agonists and other nicotinic acetylcholine receptors.

In the combination of the present invention, the compounds of the present invention and the above mentioned combination partners may be administered separately (e.g. kit of parts) or together in one pharmaceutical composition (e.g. capsule or tablet). In addition, the administration of one element of the combination of the present invention may be prior to, concurrent to, or subsequent to the administration of the other element of the combination of the present invention may be prior to, concurrent to, or subsequent to the administration of the other element of the combination. If the compounds of the present invention and the one or more additional active ingredient are present in separate formulations these separate formulations may be administered simultaneously or sequentially.

Therefore, the invention relates to the use of a compound according to the present invention in combination with at least one further active ingredient for the manufacture of a medicament for the treatment or prevention of diseases and conditions.

Numerous radioisotopes are readily available including isotopes of hydrogen, carbon, nitrogen, oxygen, phosphorus, sulfur, iodine, fluorine, bromine & chlorine. For example: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{123}$I, $^{124}$I, $^{125}$I, $^{131}$I, $^{18}$F, $^{75}$Br, $^{76}$Br, $^{77}$Br, $^{82}$Br & $^{36}$Cl.

A compound of general formula (I) can be radiolabeled by using standard techniques known in organic chemistry. Alternatively, compound of formula (I) radiolabeled with radioisotope as a substituent in one of the starting materials or in an intermediate used in the synthesis of the compound of formula (I).

Synthesis of radiolabeled compounds may be conveniently performed by a radioisotope supplier specializing in custom synthesis of radiolabeled probe compounds, such as Amersham Corporation, Arlington Heights, Ill.; Cambrige Isotopes Laboratories, Inc. Andover, Mass.; Wizard Laboratories, West Sacramento, Calif.; ChemSyn Laboratories, Lexena, Kans.; American Radiolabeled Chemicals, Inc. & St. Louis, Mo.;

Radiolabeled analogues of compound of formula (I) may be used in clinical studies to evaluate the role of $\alpha_4\beta_2$ nicotinic receptor ligands in a variety of disease areas, where $\alpha_4\beta_2$ nicotinic receptor ligands are believed to be involved.

Radiolabeled compounds of formula (I) are useful as imaging agents and biomarker for medical therapy and diagnosis. Such radiolabeled compounds are also useful as pharmacological tools for studying $\alpha_4\beta_2$ nicotinic receptor functions and activity. For example, isotopically labeled compounds are particularly useful in SPECT (single photon emission compound tomography) and in PET (positron emission tomography).

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer or from a capsule using a inhaler or insufflators. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule; it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

An effective amount of a compound of general formula (I) or their derivatives as defined above can be used to produce a medicament, along with conventional pharmaceutical auxiliaries, carriers and additives.

Such a therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

Method of Preparation

The compounds of formula (I) can be prepared by Scheme I as shown below.

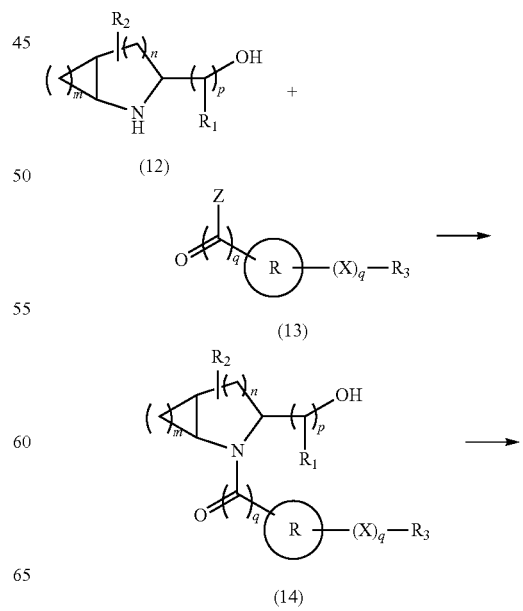

Scheme I

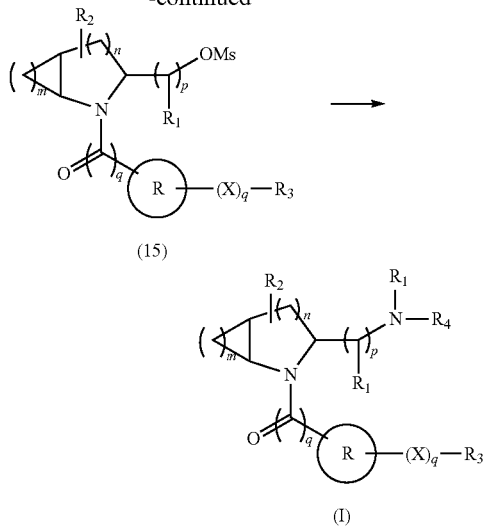

In above formula (13), the symbol "Z" represents halogen. The compound of formula (12) is reacted with a compound of formula (13) to form compound of formula (14). The hydroxyl group of formula (14) is converted to mesylate group, forming a compound of formula (15). The compound of formula (15) is treated with alkyl amines to form compound of formula (I).

In the first step of the above preparation, the compound of formula (12) is coupled with compound of formula (13) in presence of 2,2'-bis(diphenylphosphino)-1,1'-binaphthyl (BINAP) and palladium catalysts to obtain compound of formula (14). This reaction is preferably carried out in solvent such as 1,4-dioxan, tetrahydrofuran, toluene, ethyl acetate, dimethylformamide, dimethyl sulfoxide, and the like or a mixture thereof and preferably by using 1,4-dioxan. The reaction may be affected in the presence of a base such as sodium tert-butoxide, potassium tert-butoxide, potassium carbonate, sodium hydroxide, sodium hydride, cesium carbonate or mixtures thereof and preferably by using sodium tert-butoxide. The reaction is carried by using phosphino ligands such as 2,2'-bis(diphenylphosphino)-1,1'-binaphthyl, Xanthphos, dppf, cy$_3$p, Tol$_3$P or mixture thereof, preferably using 2,2'-bis(diphenylphosphino)-1,1'-binaphthyl. The palladium reagents include Pd(oAc)$_2$, Pd$_2$(dba)$_3$, Pd(dppf)Cl$_2$, Pd(pph$_3$)$_2$Cl$_2$, Pd(pph$_3$)$_4$ & Pd(dba)$_2$ and preferably Pd$_2$(dba)$_3$. The reaction temperature may range from room temperature to 150° C. based on the choice of solvent and preferably at a temperature in the range from 90° C. to 130° C. The reaction can also be carried out under microwave condition. The duration of the reaction may range from 10 to 25 hours, preferably from a period of 1 to 18 hours.

In the second step of the above preparation, the compound of formula (14) in presence of methanesulfonyl chloride is converted into compound of formula (15) in presence of base. This reaction is preferably carried out in a solvent such as 1,4-dioxan, tetrahydrofuran, triethylamine, toluene, pyridine, ethyl acetate, dichloromethane and the like or a mixture thereof and preferably by using pyridine and dichloromethane. The reaction is carried out in presence of base such as sodium carbonate, potassium carbonate, sodium bicarbonate, cesium carbonate, calcium carbonate, triethylamine or N,N-Diisopropylethylamine and the like and mixture thereof and preferably by using triethylamine. The duration of the reaction may range from 1 to 4 hours, preferably from a period of 1 to 3 hours.

In the third step of the above preparation, the compound of formula (15) is treated with alkylamine to form compound of general formula (I). This reaction is preferably carried out in a solvent such as ethanol, tetrahydrofuran, toluene, ethyl acetate, water, dimethylformamide, dimethyl sulfoxide and the like or a mixture thereof and preferably by using dimethylformamide. The duration of the reaction may range from 16 to 30 hours, preferably from a period of 22 to 26 hours.

The starting material of formula (12) is synthesized as described in preparation 1. The starting materials of formula (12) and (13) may be commercially available or can be prepared by conventional methods or by modification, using known process.

The compounds of formula (I) can also be prepared by using Scheme II as shown below Scheme II

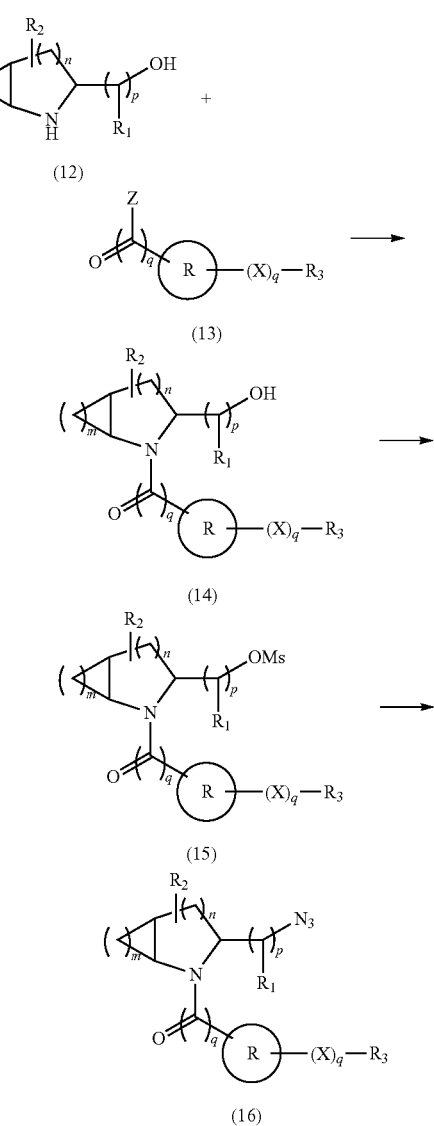

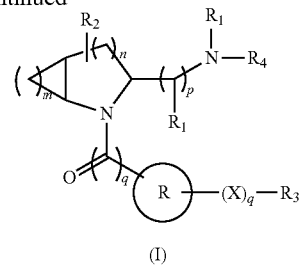

(I)

In above formula (13), the symbol "Z" represents halogen. The compound of formula (12) is reacted with a compound of formula (13) to form compound of formula (14). The hydroxyl group of formula (14) is converted to mesylate group, forming a compound of formula (15). The compound of formula (15) is treated with azide salt to form compound of formula (16). The compound of formula (16) is reduced to form compound of formula (I).

In the first step of the above preparation, the compound of formula (12) is coupled with compound of formula (13) in presence of 2,2'-bis(diphenylphosphino)-1,1'-binaphthyl (BINAP) and palladium catalysts to obtain compound of formula (14). This reaction is preferably carried out in solvent such as 1,4-dioxan, tetrahydrofuran, toluene, ethyl acetate, dimethylformamide, dimethyl sulfoxide, and the like or a mixture thereof and preferably by using 1,4-dioxan. The reaction may be affected in the presence of a base such as sodium tert-butoxide, potassium tert-butoxide, potassium carbonate, sodium hydroxide, sodium hydride, cesium carbonate or mixtures thereof and preferably by using sodium tert-butoxide. The reaction is carried by using phosphino ligands such as 2,2'-bis(diphenylphosphino)-1,1'-binaphthyl, Xanthphos, dppf, cy$_3$p, Tol$_3$P or mixture thereof, preferably using 2,2'-bis(diphenylphosphino)-1,1'-binaphthyl. The palladium reagents include Pd(OAc)$_2$, Pd$_2$(dba)$_3$, Pd(dppf)Cl$_2$, Pd(pph$_3$)$_2$Cl$_2$, Pd(pph$_3$)$_4$ & Pd(dba)$_2$ and preferably Pd$_2$(dba)$_3$. The reaction temperature may range from room temperature to 150° C. based on the choice of solvent and preferably at a temperature in the range from 90° C. to 130° C. The reaction can also be carried out under microwave condition. The duration of the reaction may range from 10 to 25 hours, preferably from a period of 1 to 18 hours.

In the second step of the above preparation, the compound of formula (14) in presence of methanesulfonyl chloride is converted into compound of formula (15) in presence of base. This reaction is preferably carried out in a solvent such as 1,4-dioxan, tetrahydrofuran, triethylamine, toluene, pyridine, ethyl acetate, dichloromethane and the like or a mixture thereof and preferably by using pyridine and dichloromethane. The reaction is carried out in presence of base such as sodium carbonate, potassium carbonate, sodium bicarbonate, cesium carbonate, calcium carbonate, triethylamine or N,N-Diisopropylethylamine and the like and mixture thereof and preferably by using triethylamine. The duration of the reaction may range from 1 to 4 hours, preferably from a period of 1 to 3 hours.

In the third step of the above preparation, the compound of formula (15) is treated with azide salt to form compound of general formula (16). This reaction is preferably carried out in a solvent such as ethanol, tetrahydrofuran, toluene, ethyl acetate, water, dimethylformamide, dimethyl sulfoxide or and the like or a mixture thereof and preferably by using dimethylformamide. The duration of the reaction may range from 2 to 20 hours, preferably from a period of 14 to 18 hours.

The reaction temperature may range from room temperature to 150° C. based on the choice of solvent and preferably at a temperature in the range from 70° C. to 110° C.

In the fourth step of the above preparation, the compound of formula (16) is reduced to form compound of general formula (I). This reaction is preferably carried out in a solvent such as ethanol, tetrahydrofuran, toluene, ethyl acetate, water, dimethylformamide, dimethyl sulfoxide and the like or a mixture thereof and preferably by using mixture of THF and water. The reaction may be affected in the presence of phosphino reagents, such as tricyclohexylphosiphine, triorthotolylphosphine, triphenyl phosphine or mixtures thereof and preferably by using triphenyl phosphine. The reaction also can be carried out under hydrogen atmosphere using palladium catalysts, Raney nickel etc. The reaction also can be carried out by using hydride reagents such as NiBH$_4$, LiAlH$_4$, DIBAL-H etc. The duration of the reaction may range from 12 to 20 hours, preferably from a period of 14 to 18 hours. The reaction temperature may range from –10° C. to 40° C. based on the choice of solvent and preferably at a temperature in the range from –5° C. to 35° C.

The starting material of formula (12) is synthesized as described in preparation 1. The starting materials of formula (12) and (13) may be commercially available or can be prepared by conventional methods or by modification, using known process.

The compounds of formula (I) can also be prepared by using Scheme III as shown below

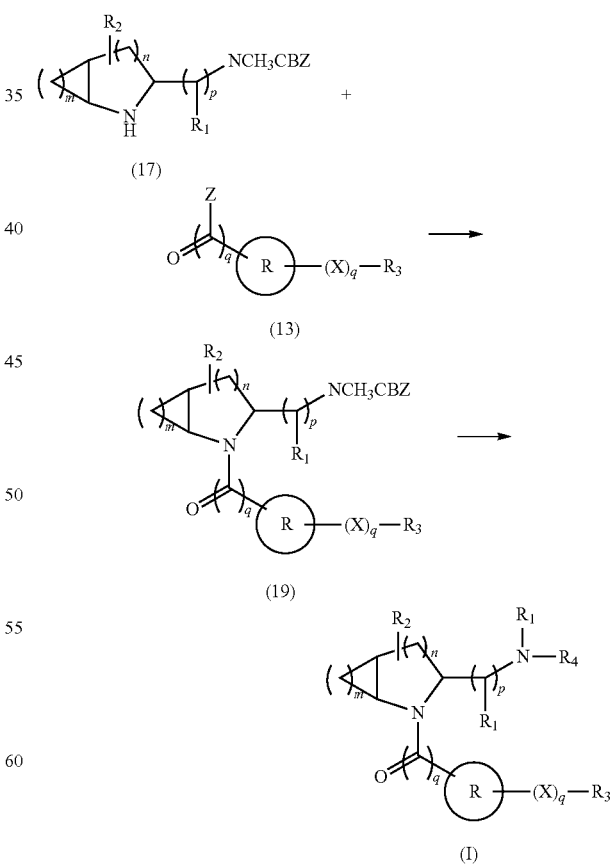

Scheme III

In above formula (13), the symbol "Z" represents halogen. The compound of formula (17) is reacted with a compound of formula (13) to form compound of formula (19). The compound of formula (19) is deprotected to form compound of formula (I).

In the first step of the above preparation, the compound of formula (17) is coupled with compound of formula (13) in presence of solvent such as dichloromethane, 1,4-dioxan, tetrahydrofuran, toluene, ethyl acetate, dimethylformamide, dimethyl sulfoxide and the like or a mixture thereof and preferably by using dichloromethane. The reaction may be affected in the presence of a base such as sodium tert-butoxide, potassium tert-butoxide, potassium carbonate, sodium hydroxide, sodium hydride, cesium carbonate, diisopropylethylamine, triethylamine or mixtures thereof and preferably by using diisopropylethylamine. The reaction temperature may range from 20° C. to 40° C. based on the choice of solvent and preferably at a temperature in the range from 25° C. to 35° C. The duration of the reaction may range from 0.5 to 2 hours, preferably from a period of 1 to 1.5 hours. Additional catalysts like 4-Dimethylaminopyridine (DMAP) can be used optionally.

In the second step of the above preparation, the compound of formula (19) is deprotected to form compound of formula (I) in presence of solvent such as ethanol, tetrahydrofuran, toluene, ethyl acetate, dimethylformamide, dimethyl sulfoxide and the like or a mixture thereof and preferably by using ethanol. The reaction is carried out under hydrogen atmosphere using palladium catalysts. The duration of the reaction may range from 1 to 5 hours, preferably from a period of 2 to 4 hours. The reaction temperature may range from 20° C. to 40° C. based on the choice of solvent and preferably at a temperature in the range from 25° C. to 35° C.

The starting material of formula (17) is synthesized as described in preparation 2. The starting materials of formula (17) and (13) can also be prepared by conventional methods or by modification, using known process.

Compounds obtained by the above method of preparation of the present invention can be transformed into another compound of this invention by further chemical modifications using well-known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.
If necessary, any one or more than one of the following steps can be carried out:
i) converting a compound of the formula (I) into another compound of the formula (I)
ii) removing any protecting groups; or
iii) forming a pharmaceutically acceptable salt, solvate or a prodrug thereof.

Process (i) may be performed using conventional interconversion procedures such as epimerisation, oxidation, reduction, alkylation, and nucleophilic or electrophilic aromatic substitution and ester hydrolysis or amide bond formation.

In process (ii) suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (eg. benzyl), which may be removed by hydrolysis (e.g. using an acid such as hydrochloric or trifluoroacetic acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl, which may be removed by base catalyzed hydrolysis or a solid phase resin bound benzyl group, such as a Merrifield resin bound 2,6-dimethoxybenzyl group (Ellman linker), which may be removed by acid catalyzed hydrolysis, for example with trifluoroacetic acid.

In process (iii) pharmaceutically acceptable salts may be prepared conventionally by reaction with the appropriate acid or acid derivative as described earlier in detail.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of compound of general formula (I) containing a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) one or more of the reagents may be used in their optically active form.
ii) optically pure catalyst or chiral ligands along with metal catalyst may be employed in the reduction process. The metal catalyst may be Rhodium, Ruthenium, Indium and the like. The chiral ligands may preferably be chiral phosphines
iii) the mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative
iv) the mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid and organic acids e.g. succinic, maleic, acetic, fumaric, citric, malic, tartaric, benzoic, p-toluic, p-toluenesulfonic, methanesulfonic or naphthalenesulfonic acid. The present invention includes, within its scope, all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

EXAMPLES

The novel compounds of the present invention were prepared according to the following procedures, using appropriate materials and are further exemplified by the following specific examples. The most preferred compounds of the invention are any or all of those specifically set forth in these examples. These compounds are not, however, to be construed as forming the only genus that is considered as the invention and any combination of the compounds or their moieties may itself form a genus. The following examples further illustrate details for the preparation of the compounds of the present invention. Those skilled in the art will readily understand that known variations of the conditions and process of the following preparative procedures can be used to prepare these compounds.

Preparation 1: Preparation of [2-(5-Bromopyridin-3-yl)-2-azabicyclo[3.1.0]hex-3-yl]methanol Step (i): Preparation of 5-(tert-Butyldiphenylsilanyloxymethyl)pyrrolidin-2-one To an ice cold solution of 5-hydroxymethylpyrrolidin-2-one (5 grams, 43.4 mmol) in dichloromethane (174 mL) was added imidazole (6.5 grams, 95.5 mmol), 4-dimethylaminopyridine (530 mg, 4.3 mmol) followed by tert-butyldiphenylsilyl chloride (12.53 grams, 45.57 mmol). The reaction mixture was gradually warmed to room temperature and stirred for 2 hours. The reaction mixture was diluted with dichloromethane, washed with water, brine and dried over anhydrous sodium sulfate. The solvent was removed under reduced pressure to obtain title compound of 15.37 grams, as gummy liquid, which was taken up for the next reaction without further purification.

$^1$H-NMR (CDCl$_3$): 7.65-7.63 (m, 4H), 7.45-7.37 (m, 6H), 3.84-3.77 (m, 1H), 3.62 (dd, J=3.9, 10.2 Hz, 1H), 3.50 (dd, J=7.7, 10.2 Hz, 1H), 2.40-2.30 (m, 2H), 2.20-2.11 (m, 1H), 1.76-1.67 (m, 1H), 1.05 (s, 9H);
Mass (m/z): 354 [M+H$^+$].

Step (ii): Preparation of 2-(tert-Butyldiphenylsilanyloxymethyl)-5-oxo-pyrrolidine-1-carboxylic acid tert-butyl ester To a stirred solution of above obtained compound (15.35 grams, 43.42 mmol) in acetonitrile (174 mL) was added 4-dimethylaminopyridine (6.36 grams, 52.1 mmol) and tert-butyldicarbonate (11.0 mL, 47.8 mmol). After stirring for 16, hours at room temperature the reaction mixture was diluted with ethyl acetate, washed with water, brine and dried over anhydrous sodium sulfate. The solvent was removed under reduced pressure and the crude product was purified by flash column chromatography using 230-400 mesh silica gel to obtain title compound of 18.28 grams as solid. Yield: 93% for two steps Melting Range: 105.9-108.3° C.
IR (cm$^{-1}$): 2953, 2930, 1747, 1709, 1471, 1431, 1311, 1111, 742, 705;
$^1$H-NMR (CDCl$_3$): 7.64-7.56 (m, 4H), 7.46-7.35 (m, 6H), 4.22-4.19 (m, 1H), 3.89 (dd, J=4.2, 10.5 Hz, 1H), 3.70 (dd, J=2.3, 10.5 Hz, 1H), 2.78 (ddd, J=10.4, 10.4, 17.6 Hz, 1H), 2.44 (ddd, J=3.2, 8.8, 17.6 Hz, 1H), 2.22-2.07 (m, 2H), 1.43 (s, 9H), 1.04 (s, 9H);
Mass (m/z): 454 [M+H$^+$].

Step (iii): Preparation of 2-(tert-Butyldiphenylsilanyloxymethyl)-5-hydroxy pyrrolidine-1-carboxylic acid tert-butyl ester To the stirred solution of above obtained compound (18.27 grams, 40.28 mmol) in tetrahydrofuran (160 mL) at −78° C., was added a solution of lithiumtriethylborohydride (1M in tetrahydrofuran, 44.3 mL). After stirring for 1 hour, the reaction mixture was quenched by adding saturated solution of sodiumbicarbaonate (68 mL). The reaction mixture was warmed to 0° C., hydrogen peroxide (30% w/v, 1.3 mL) was added and was stirred for 20 minutes. The two layers were separated, the aqueous layer was extracted with dichloromethane and the combined organic layer was dried over anhydrous sodium sulfate. The solvent was removed under reduced pressure to obtain title compound of 20.0 grams as gummy liquid, which was sufficiently pure to take up for the next reaction. Yield: 95.7%.

IR (cm$^{-1}$): 3444, 2960, 2931, 1681, 1392, 1166, 1112, 702;
$^1$H-NMR (CDCl$_3$): 7.71-7.60 (m, 4H), 7.45-7.32 (m, 6H), 5.52-5.43 (m, 1H), 4.05-3.96 (m, 1H), 3.90-3.82 (m, 1H), 3.75-3.52 (m, 2H), 2.25-2.15 (m, 1H), 2.10-1.82 (m, 3H), 1.51 (s, 3H), 1.34 (s, 6H), 1.06 (s, 9H);
Mass (m/z): 456 [M+H$^+$].

Step (iv): Preparation of 2-(tert-Butyldiphenylsilanyloxymethyl)-5-methoxypyrrolidine-1-carboxylic acid tertbutyl ester To an ice-cold solution of above obtained compound (18.34 grams, 40.2 mmol) in methanol (160 mL), was added pyridiniumparatoluene sulfonate (p-PTS, 1.0 gram, 4.02 mmol). The reaction mixture was gradually warmed to room temperature and stirred for 2 hours. Triethylamine (1.2 mL, 8.04 mmol) was added and the volatiles were removed under reduced pressure and the crude product was purified by flash column using 230-400 mesh silica gel to obtain isomeric mixture of title compound of 18.1 grams as gummy liquid. Yield: 95.7%.

IR (cm$^{-1}$): 2958, 2931, 1701, 1390, 1366, 1163, 1112, 1085, 757, 702;
$^1$H-NMR (CDCl$_3$): 7.70-7.65 (m, 4H), 7.45-7.35 (m, 6H), 5.28-5.12 (m, 1H), 4.05-3.85 (m, 2H), 3.70-3.50 (m, 1H), 3.26 (s, 3H), 2.25-2.05 (m, 2H), 1.95-1.85 (m, 1H), 1.80-1.70 (m, 1H), 1.45 (s, 3H), 1.33 (s, 6H), 1.05 (s, 9H);
Mass (m/z): 492 [M+Na$^+$].

Step (v): Preparation of 2-(tert-Butyldiphenylsilanyloxymethyl)-2,3-dihydropyrrole-1-carboxylic acid tert-butyl ester A mixture of above obtained compound (18.1 grams, 38.5 mmol) and ammonium chloride (311 mg, 5.7 mmol) was heated at 150° C. under reduced pressure (50 mbar) for 1 hour.

The reaction mixture was cooled to room temperature and purified by flash column using 230-400 mesh silica gel to obtain title compound of 14.6 grams as gummy liquid. Yield: 86.5%.

IR (cm$^{-1}$): 2959, 2930, 2857, 1701, 1404, 1132, 1112, 762, 741, 701;

$^1$H-NMR (CDCl$_3$): 7.66-7.60 (m, 4H), 7.45-7.32 (m, 6H), 6.49 (d, J=43.3 Hz, 1H), 4.95 (d, J=34.1 Hz, 1H), 4.25 (d, J=42.0 Hz, 1H), 3.90-3.58 (m, 2H), 2.90-2.65 (m, 2H), 1.46 (s, 3H), 1.32 (s, 6H), 1.04 (s, 9H);

Mass (m/z): 438 [M+H$^+$].

Step (vi): Preparation of 3-(tert-Butyldiphenylsilanyloxymethyl)-2-azabicyclo[3.1.0]hexane-2-carboxylic acid tert-butyl ester To an ice cold solution of above obtained compound (2.0 grams, 4.56 mmol) in dichloromethane (18 mL) was added a solution of diethylzinc (1M in hexane, 5.0 mL), followed by diiodomethane (0.55 mL, 6.84 mmol) over a period of 15 minutes and stirred for 30 minutes. The reaction mixture was gradually warmed to room temperature and stirred for 3 hours. The pH of the reaction mixture was adjusted to 8 by addition of saturated sodium bicarbonate solution. Two layers were separated and the aqueous layer was extracted with dichloromethane. The combined organic layer was washed with brine, dried over anhydrous sodium sulfate and the solvent was evaporated under reduced pressure and the crude product was purified by flash column chromatography using 230-400 mesh silica gel to obtain to obtain title compound of 1.5 grams as gummy liquid. Yield: 73%.

IR (cm$^{-1}$): 2960, 2931, 2857, 1698, 1391, 1178, 1130, 1112, 1090, 702;

$^1$H-NMR (CDCl$_3$): 7.68-7.62 (m, 4H), 7.44-7.32 (m, 6H), 3.90-3.80 (m, 1H), 3.74-3.68 (m, 2H), 3.22-3.13 (m, 1H), 2.40-2.27 (m, 1H), 2.08-1.96 (m, 1H), 1.52-1.48 (m, 1H), 1.40 (s, 9H), 1.05 (s, 9H), 0.90-0.80 (m, 1H), 0.38-0.30 (m, 1H);

Mass (m/z): 452 [M+H$^+$].

Step (vii): Preparation of 3-Hydroxymethyl-2-azabicyclo[3.1.0]hexane-2-carboxylic acid tert-butyl ester To an ice cold solution of above obtained compound (16.8 grams, 37.1 mmol) in dry tetrahydrofuran (104 mL) was added tetrabutylammonium fluoride (1M in tetrahydrofuran, 37.1 mL) over a period of 10 minutes. The reaction mixture was gradually warmed to room temperature and stirred for 12 hours. The volatiles were removed under reduced pressure and the crude product was purified by flash column chromatography to obtain title compound of 7.0 grams as gummy liquid. Yield: 88.6%.

IR (cm$^{-1}$): 3417, 2976, 2878, 1694, 1669, 1403, 1255, 1175, 1133, 1085, 773;

$^1$H-NMR (CDCl$_3$): 4.90 (bs, 1H), 3.75-3.65 (m, 1H), 3.63-3.55 (m, 2H), 3.27 (ddd, J=2.3, 6.2, 8.5 Hz, 1H), 2.16 (dd, J=8.3, 13.1 Hz, 1H), 1.82-1.70 (m, 1H), 1.52-1.44 (m, 1H), 1.49 (s, 9H), 0.78-0.68 (m, 1H), 0.43-0.35 (m, 1H);

Mass (m/z): 214 [M+H$^+$].

Step (viii): Preparation of (2-Azabicyclo[3.1.0]hex-3-yl)methanol

To an ice-cold solution of 3-Hydroxymethyl-2-azabicyclo[3.1.0]hexane-2-carboxylic acid tert-butyl ester (obtained in preparation 1) (6.5 grams, 14.41 mmol) in isopropanol (7 mL), a solution of dry hydrochloride in isopropanol (3 M, 28 mL) was added, the reaction mixture was gradually warmed to room temperature and stirred for 16 hours. The reaction mixture was diluted with a solution of ammonia in methanol (7 M, 14 mL) and the volatiles were removed under reduced pressure. The crude product was purified by 230-400 silica gel flash column chromatography to obtain title compound of 1.51 grams. Yield: 93%.

IR (cm$^{-1}$): 3348, 2934, 2866, 1666, 1398, 1086, 1044, 1021, 816, 758;

$^1$H NMR (CDCl$_3$): 3.57 (dd, J=3.6, 10.9 Hz, 1H), 3.42 (dd, J=4.6, 10.9 Hz, 1H), 3.15-3.07 (m, 1H), 2.82-2.74 (m, 1H), 1.94-1.80 (m, 2H), 1.46-1.38 (m, 1H), 0.52-0.47 (m, 1H), 0.46-0.38 (m, 1H);

Mass (m/z): 114 [M+H$^+$].

Step (ix): Preparation of [2-(5-Bromopyridin-3-yl)-2-azabicyclo[3.1.0]hex-3-yl]methanol To a stirred solution of (2-Azabicyclo[3.1.0]hex-3-yl) methanol (750 mg, 6.63 mmol) (obtained in step (i)) in dry 1,4-dioxan (20 mL) in a pressure reaction vessel was added 3,5-dibromopyridine (1.57 grams, 6.63 mmol), sodium tert-butoxide (700 mg, 7.3 mmol) and racemic-2,2'-bis(diphenylphosphino)-1,1'-binaphthyl (207 mg, 0.33 mmol). The reaction mixture was degassed for 30 minutes, then tris (dibenzylideneacetone)dipalladium (0) (122 mg, 0.133 mmol) was added. The screw cap was fixed on the reaction vessel, the temperature of the reaction was gradually increased to 110° C. and the reaction mixture was stirred at this temperature for 16 hours. The reaction mixture was cooled to room temperature diluted with saturated sodium bicarbonate and extracted with ethyl acetate. The combined organic layer was dried over anhydrous sodium sulfate, the solvent was removed under reduced pressure and the crude product was purified by 230-400 silica gel flash column chromatography to obtain title compound of 600 mg as solid. Yield: 33%.

Melting range: 90.4-93.5° C.

IR (cm$^{-1}$): 3242, 2934, 2893, 1573, 1538, 1456, 1379, 1193, 1004, 688, 573;

$^1$H-NMR (CDCl$_3$): 8.19 (s, 1H), 8.04 (s, 1H), 7.31 (s, 1H), 3.80-3.62 (m, 3H), 3.15-3.07 (m, 1H), 2.25-2.15 (m, 1H), 2.10 (dd, J=7.7, 13.0 Hz, 1H), 1.82-1.72 (m, 1H), 1.05-0.96 (m, 1H), 0.28-0.21 (m, 1H);

Mass (m/z): 269, 271 [M+H$^+$].

Preparation 2: Preparation of 3-[N-(Benzyloxycarbonyl)-N-(methyl)aminomethyl]-2-azabicyclo[3.1.0] hexane Step (i): Preparation of 3-Methanesulfonyloxymethyl-2-azabicyclo[3.1.0]hexane-2-carboxylic acid tert-butyl ester To an ice-cold solution of 3-Hydroxymethyl-2-azabicyclo [3.1.0]hexane-2-carboxylic acid tert-butyl ester (2.52 grams, 11.83 mmol) in dry dichloromethane (10 mL) was added triethylamine (2.5 mL, 17.75 mmol) followed by methanesulfonyl chloride (1.0 mL, 13.01 mmol). The reaction mixture was gradually warmed to room temperature and stirred for 1 hour. The reaction mixture was diluted with dichloromethane. Organic layer was washed with saturated sodium bicarbonate solution followed brine, dried over anhydrous sodium sulfate and the solvent was evaporated under reduced pressure and the crude product was purified by flash column chromatography using 230-400 mesh silica gel to obtain title compound, 3.09 grams as gummy liquid. Yield: 90%.

¹H-NMR (CDCl₃): 4.45-4.20 (m, 2H), 3.98-3.90 (m, 1H), 3.30-3.20 (m, 1H), 3.02 (s, 3H), 2.28-2.08 (m, 2H), 1.65-1.55 (m, 1H), 1.48 (s, 9H), 0.95-0.85 (m, 1H), 0.47-0.40 (m, 1H);

Mass (m/z): 292 [M+H⁺].

Step (ii): Preparation of 3-Methylaminomethyl-2-azabicyclo[3.1.0]hexane-2-carboxylic acid tert-butyl ester To a stirred solution of above obtained compound (3.09 grams, 10.61 mmol) in dimethylformamide (23 mL) was added 40% (w/v) aqueous dimethylamine solution (23 mL). Upon stirring for 24 hours, the reaction mixture was diluted with saturated sodium chloride solution (150 mL) and a 2.5 M sodium hydroxide solution (23 mL) and extracted with ethyl acetate. The combined organic layer was dried over anhydrous sodium sulfate and the solvent was removed under reduced pressure and the crude product was purified by 230-400 silica gel flash column chromatography to get desired compound of 1.95 grams. Yield: 85%.

IR (cm⁻¹): 3396, 3322, 2959, 2928, 1629, 1592, 1485, 1389, 1195, 1044, 955, 861, 770;

¹H-NMR (CDCl₃): 3.90-3.80 (m, 1H), 3.40-3.28 (m, 2H), 2.98-2.88 (m, 1H), 2.84 (s, 3H), 2.55-2.45 (m, 1H), 1.90-1.80 (m, 1H), 1.60-1.50 (m, 1H), 1.50 (s, 9H), 0.78-0.68 (m, 1H), 0.57-0.52 (m, 1H);

Mass (m/z): 227 [M+H⁺].

Step (iii): Preparation of t-Butyl 3-[N-(Benzyloxycarbonyl)-N-(methyl)aminomethyl]-2-azabicyclo[3.1.0]hexane-2-carboxylate To an ice-cold solution of above obtained compound (2.0 grams, 8.85 mmol) in dry tetrahydrofuran (35 mL) was added anhydrous potassium carbonate (1.84 grams, 13.3 mmol) followed by benzyl chloroformate 50% w/v solution in toluene (3.4 mL, 9.74 mmol). The reaction mixture was gradually warmed to room temperature and stirred for 16 hours at room temperature. The reaction mixture was diluted with water and aqueous layer was extracted with dichloromethane. The combined organic layer was washed with brine, dried over anhydrous sodium sulfate and the solvent was evaporated under reduced pressure and the crude product was purified by flash column chromatography using 230-400 mesh silica gel to obtain title compound of 2.0 grams as gummy liquid. Yield: 63%.

IR (cm⁻¹): 2958, 2930, 1697, 1586, 1404, 1252, 1175, 1127, 1085, 755;

¹H-NMR (CDCl₃): 7.45-7.28 (m, 5H), 5.14 (s, 2H), 4.10-4.0 (m, 1H), 3.67-3.30 (m, 2H), 3.25-3.05 (m, 1H), 2.96 (s, 3H), 2.18-1.85 (m, 2H), 1.46-1.40 (m, 1H) 1.46 (s, 9H), 0.95-0.85 (m, 1H), 0.40-0.30 (m 1H);

Mass (m/z): 361 [M+H⁺].

Step (iv): Preparation of 3-[N-(Benzyloxycarbonyl)-N-(methyl)aminomethyl]-2-azabicyclo[3.1.0]hexane To an ice-cold solution of above obtained compound (1.8 grams, 5.0 mmol) in dry dichloromethane (5 mL) was added trifluroacetic acid (5 mL). The reaction mixture was gradually warmed to room temperature and stirred for 6 hours at room temperature. Evaporated volatiles under reduced pressure, residue diluted with dichloromethane. Organic layer was washed with saturated sodium bicarbonate solution followed brine, dried over anhydrous sodium sulfate and the solvent was evaporated under reduced pressure and the crude product was purified by flash column chromatography using 230-400 mesh silica gel to obtain title compound of 1.09 grams. Yield: 85%.

IR (cm⁻¹): 3316, 2931, 1699, 1585, 1485, 1402, 1300, 1151, 1079, 767, 742;

¹H-NMR (CDCl₃): 7.42-7.28 (m, 5H), 5.12 (s, 2H), 3.45-3.35 (m, 1H), 3.30-3.05 (m, 2H), 2.98 (s, 3H), 2.82-2.72 (m, 1H), 2.05-1.88 (m, 1H) 1.60-1.55 (m, 1H), 1.45-1.35 (m, 1H), 0.60-0.50 (m 1H), 0.38-0.30 (m, 1H);

Mass (m/z): 261 [M+H⁺].

Example 1

Preparation of N-[2-(5-Bromopyridin-3-yl)-2-azabicyclo[3.1.0]hex-3-ylmethyl]-dimethylamine hydrochloride Step (i): Preparation of 2-(5-bromopyridin-3-yl)-2-azabicyclo[3.1.0]hex-3-ylmethyl methanesulfonate To an ice-cold solution of [2-(5-Bromopyridin-3-yl)-2-azabicyclo[3.1.0]hex-3-yl]methanol (462 mg, 2.43 mmol) in dry dichloromethane (10 mL) was added triethylamine (0.51 mL, 3.6 mmol) followed by methanesulfonyl chloride (334 mg, 2.92 mmol). The reaction mixture was gradually warmed to room temperature and stirred for 1 hour. The volatiles were removed under reduced pressure and the crude product was purified by flash column chromatography to obtain title compound of 586 mg as gummy liquid. Yield: 90%.

¹H-NMR (CDCl₃): 8.14 (s, 1H), 8.06 (s, 1H), 7.26 (s, 1H), 4.30 (dd, J=5.8, 10.2 Hz, 1H), 4.20 (dd, J=6.6, 10.2 Hz, 1H), 4.30-3.60 (m, 1H), 3.10-3.18 (m, 1H), 3.0 (s, 3H), 2.28-2.10 (m, 2H), 1.88-1.78 (m, 1H), 1.60-1.50 (m, 1H), 1.13-1.05 (m, 1H);

Mass (m/z): 347, 349 [M+H⁺].

Step (ii): Preparation of N-[2-(5-Bromopyridin-3-yl)-2-azabicyclo[3.1.0]hex-3-ylmethyl]dimethylamine hydrochloride To a stirred solution of above compound (560 mg, 2.09 mmol) in dimethylformamide (4 mL) was added 40% (w/v) aqueous dimethylamine solution (4 mL). Upon stirring for 24 hours, the reaction mixture was diluted with saturated sodium chloride solution (30 mL) and a 2.5 M sodium hydroxide solution (4 mL) and extracted with ethyl acetate. The combined organic layer was dried over anhydrous sodium sulfate and the solvent was removed under reduced pressure and the crude product was purified by 230-400 silica gel flash column chromatography. The product, thus obtained was stirred with dry hydrochloric acid in isopropanol (3 M, 4 mL) for 10 minutes, the volatiles were removed under reduced pressure and the residue was triturated with ether to obtain title compound of 215 mg, Yield: 40%.

IR (cm⁻¹): 3408, 2943, 2820, 2768, 1677, 1573, 1458, 1370, 1099, 997;

¹H-NMR (DMSO): 9.96 (bs, 1H), 8.2 (s, 1H), 8.04 (s, 1H), 7.47 (s, 1H), 4.20-4.10 (m, 1H), 3.40-3.22 (m, 3H), 2.87 (d, J=4.6 Hz, 3H), 2.83 (d, J=4.6 Hz, 3H), 2.35 (dd, J=7.1, 13.1 Hz, 1H), 2.10 (dd, J=7.9, 13.1 Hz, 1H), 1.84-1.77 (m, 1H), 1.0-0.92 (m, 1H), 0.28-0.21 (m, 1H);

Mass (m/z): 296, 298 [M+H⁺].

Example 2

Preparation of [2-(5-Bromopyridin-3-yl)-2-azabicyclo[3.1.0]-hex-3-yl]-methylamine Step (i): Preparation of 3-Azidomethyl-2-(5-bromopyridin-3-yl)-2-azabicyclo[3.1.0]hexane To a stirred solution of methane sulfonate (as obtained in Step (i) of Example 1) (215 mg, 0.62 mmol) in dry dimethylfuran (2 mL) was added sodium azide (180 mg, 2.77 mmol). The reaction mixture was gradually heated to 90° C. and stirred for 16 hours. Upon completion of the reaction, it was diluted with ether, washed with water, brine, dried over anhydrous sodium sulfate and the solvent was removed under reduced pressure. The crude product was purified by silica gel flash column chromatography to obtain the title compound as gummy liquid of 164 mg. Yield: 90%.

$^1$H-NMR (CDCl$_3$): 8.14 (d, J=2.5 Hz, 1H), 8.0 (d, J=2.0 Hz, 1H), 7.25 (m, 1H), 3.90-3.80 (m, 1H), 3.44 (dd, J=5.7, 8.3 Hz, 2H), 3.18-3.12 (m, 1H), 2.25-2.15 (m, 2H), 1.90-1.80 (m, 1H), 1.12-1.03 (m, 1H), 0.33-0.28 (m, 1H);

Mass (m/z): 294, 296 [M+H$^+$].

Step (ii): Preparation of [2-(5-Bromopyridin-3-yl)-2-azabicyclo-[3.1.0]-hex-3-yl]methylamine To a stirred solution of above compound (175 mg, 0.6 mmol) in tetrahydrofuran at ice cold temperature was added triphenylphosphine (173 mg, 1.06 mmol) and water (32 µL, 1.8 mmol). The reaction mixture was gradually warmed to room temperature and stirred for 16 hours. The volatiles were removed under reduced pressure and the crude product was purified by silica gel flash column chromatography to obtain title compound of 98 mg. Yield: 63%.

IR (cm$^{-1}$): 3584, 3365, 2935, 2871, 1572, 1458, 1370, 1237, 1202, 1101, 996, 841;

$^1$H-NMR (CDCl$_3$): 8.15 (d, J=2.5 Hz, 1H), 8.01 (d, J=2.0 Hz, 1H), 7.25 (m, 1H), 3.75-3.65 (m, 1H), 3.17-3.10 (m, 1H), 2.90 (d, J=5.5 Hz, 2H), 2.25-2.10 (m, 2H), 1.85-1.75 (m, 1H), 1.10-1.0 (m, 1H), 0.30-0.24 (m, 1H);

Mass (m/z): 268, 270 [M+H$^+$].

Examples 3

Preparation of Furan-2-yl-(3-methylaminomethyl-2-aza bicyclo[3.1.0]hex-2-yl)methanone tartarate (Isomers)

Step (i): Preparation of Furan-2-yl-[3-[(N-Benzyloxycarbonyl-N-Methyl)aminomethyl]-2-azabicyclo[3.1.0]hex-2-yl]methanone To a stirred solution of 3-[N-(Benzyloxycarbonyl)-N-(methyl)aminomethyl]-2-azabicyclo[3.1.0]hexane (210 mg, 0.81 mmol) in dichloromethane (2 mL) cooled at 0° C. under inert atmosphere was added diisopropylethylamine (0.42 mL, 2.4 mmol), 4-Dimethylaminopyridine (0.1 mmol) and a solution of acid chloride (0.09 mL, 0.89 mmol) in dichloromethane (2 mL) over a period of 30 minutes. The reaction mixture was gradually warmed to room temperature and stirred for 1 hour. Upon completion of the reaction, it was diluted with cold water and extracted with dichloromethane. The combined organic layer was dried over anhydrous sodium bisulphate and the solvent was removed under reduced pressure. The crude product was purified by silica gel flash column chromatography to obtain 206 mg as the mixture of two isomers. Yield: 73%.

IR (cm$^{-1}$): 2936, 1699, 1626, 1484, 1406, 1300, 1198, 1142, 1066, 700;

$^1$H-NMR (CDCl$_3$): 7.55 (s, 1H), 7.40-7.30 (m, 5H), 7.20 (s, 0.5H), 7.17 (s, 0.5H), 6.50 (s, 1H), 5.12 (s, 2H), 4.73-4.62 (m, 1H), 3.70-3.50 (m, 3H), 3.01 (s, 3H), 2.22-2.0 (m, 1H), 1.96-1.65 (m, 2H) 1.20-1.02 (m, 1H), 0.61-0.52 (m 1H).

Mass (m/z): 355 [M+H$^+$].

Step (ii): Preparation of Furan-2-yl-(3-methylaminomethyl-2-aza bicyclo[3.1.0]hex-2-yl)methanone tartarate (Isomers)

To a stirred solution of Furan-2-yl-[3-[(N-Benzyloxycarbonyl-N-Methyl)aminomethyl]-2-azabicyclo[3.1.0]hex-2-yl]methanone (124 mg, 0.35 mmol) in ethanol (2 mL) under hydrogen atmosphere was added Palladium on carbon (13 mg, 10% w/w). The reaction mixture was filtered after stirring for at room temperature for 3 hours. The solvent was removed under reduced pressure and the crude product was purified by silica gel flash column chromatography to obtain two isomers of Furan-2-yl-(3-methylaminomethyl-2-aza bicyclo[3.1.0]hex-2-yl)methanone tartarate (20 mg and 36 mg respectively). Yield: 73%.

Characterization data of Furan-2-yl-(3-methylaminomethyl-2-aza bicyclo[3.1.0]hex-2-yl) methanone tartarate (Isomer-1)

IR (cm$^{-1}$): 3377, 2925, 1627, 1595, 1486, 1379, 1198, 1082, 955, 861;

$^1$H-NMR (CD$_3$OD): 7.73 (d, J=1.8 Hz, 1H), 7.16 (d, J=3.5 Hz, 1H), 6.61 (dd, J=3.5, 1.8 Hz, 1H), 4.42 (s, 2H), 4.12-4.02 (m, 1H), 3.68-3.58 (m, 1H), 3.33 (s, 3H), 3.30-3.15 (m, 2H), 2.35-2.25 (m, 1H), 2.07-1.95 (m, 1H), 1.90-1.82 (m, 1H), 1.10-1.0 (m, 1H), 0.90-0.80 (m, 1H);

Mass (m/z): 221 [M+H$^+$].

Characterization data of Furan-2-yl-(3-methylaminomethyl-2-aza bicyclo[3.1.0]hex-2-yl)methanone tartarate (Isomer-2)

IR (cm$^{-1}$): 3408, 2955, 1623, 1596, 1486, 1460, 1378, 1197, 1081, 956, 861;

$^1$H-NMR (CD$_3$OD): 7.81 (s, 1H), 7.44 (d, J=3.2 Hz, 1H), 6.68 (d, J=3.2 Hz, 1H), 4.80-4.70 (m, 1H), 4.43 (s, 2H), 3.82 (dd, J=11.8, 3.2 Hz, 1H), 3.80-3.72 (m, 1H), 3.63 (dd, J=11.8, 6.8 Hz, 1H), 2.75 (s, 3H), 2.28-2.15 (m, 1H), 2.12-2.02 (m, 1H), 1.97-1.88 (m, 1H), 0.98-0.85 (m, 1H), 0.80-0.72 (m, 1H);

Mass (m/z): 221 [M+H$^+$].

Examples 4-39

The compounds of Examples 4-39 were prepared by following the procedures as described in Examples 1 to 3, with some non-critical variations

| | | |
|---|---|---|
| 4. | N-[2-(Pyridin-3-yl)-2-azabicyclo[3.1.0]hex-3-ylmethyl]methylamine hydrochloride (7:3 mix of two rotamers) | IR (cm$^{-1}$): 3287, 2935, 2856, 1667, 1582, 1489, 1428, 1362, 1247, 1116, 1008, 792, 707; $^1$H-NMR (CDCl$_3$): 8.32 (s, 0.7H), 8.26 (s, 0.3H), 8.0-7.94 (m, 1H), 7.15-7.05 (m, 2H), 3.80-3.72 (m, 1H), 3.58 (dd, J = 3.3, 12.0 Hz, 0.7H), 3.15-3.07 (m, 0.3H), 2.85-2.70 (m, 0.7H), 2.70-2.60 (m, 0.3H), 2.48 (s, 3H), 2.48-2.40 (m, 1H), 2.20-2.02 (m, 1H), 1.70-1.60 (m, 1H), 1.50-1.40 (m, 1H), 1.0-0.90 (m, 1H), 0.25-0.15 (m, 1H); Mass (m/z): 204 [M + H$^+$]. |
| 5. | N-[2-(5-Bromopyridin-3-yl)-2- | $^1$H-NMR (CD$_3$OD): 8.24 (s, 0.6H), 8.16 (s, 0.4H), 8.01 (s, 0.4H), 7.98 (s, 0.6H), 7.57 (s, 0.6H), 7.52 (s, 0.4H), 4.42 (s, 2H), |

| | | |
|---|---|---|
| azabicyclo[3.1.0]hex-3-ylmethyl]ethylamine tartarate (2:3 mix of two rotamers) | 4.15-4.05 (m, 0.4H), 3.88-3.78 (m, 0.6H), 3.20-3.0 (m, 4H), 2.85-2.74 (m, 1H), 2.28-2.20 (m, 1H), 1.92-1.85 (m, 1H), 1.62-1.56 (m, 1H), 1.45-1.28 (m, 3H), 1.15-1.05 (m, 1H), 0.38-0.26 (m, 1H); Mass (m/z): 296, 298 [M + H$^+$]. | |
| 6. 2-(5-Bromopyridin-3-yl)-3-pyrrolidin-1-ylmethyl-2-azabicyclo[3.1.0]hexane tartarate | IR (cm$^{-1}$): 3434, 2961, 1733, 1577, 1458, 1244, 1206, 1124, 1076, 835, 690, 670; $^1$H-NMR (CD$_3$OD): 8.14 (s, 1H), 8.01 (s, 1H), 7.51 (s, 1H), 4.45 (s, 2H), 4.28-4.20 (m, 1H), 3.50-3.20 (m, 7H), 2.30-2.18 (m, 2H), 2.12-2.01 (m, 4H), 1.98-1.90 (m, 1H), 1.14-1.05 (m, 1H), 0.38-0.30 (m, 1H); Mass (m/z): 322, 324 [M + H$^+$]. | |
| 7. 2-(5-Bromopyridin-3-yl)-3-(morpholin-4-ylmethyl)-2-azabicyclo[3.1.0]hexane tartarate | IR (cm$^{-1}$): 3432, 2929, 2873, 1734, 1724, 1578, 1462, 1262, 1121, 1080 974, 844, 678; $^1$H-NMR (CD$_3$OD): 8.21 (s, 1H), 7.91 (s, 1H), 7.52 (s, 1H), 4.50 (s, 2H), 3.93-3.87 (m, 1H), 3.86-3.75 (m, 2H), 3.40-3.35 (m, 2H), 3.30-3.20 (m, 1H), 3.02-2.80 (m, 4H), 2.80-2.72 (m, 1H), 2.62-2.56 (m, 1H), 2.30-2.21 (m, 1H), 2.10-2.01 (m, 1H), 1.65-1.56 (m, 1H), 1.09-1.0 (m, 1H), 0.28-0.20 (m, 1H); Mass (m/z): 338, 340 [M + H$^+$]. | |
| 8. 2-(5-Bromopyridin-3-yl)-3-(piperazin-1-ylmethyl)-2-azabicyclo[3.1.0]hexane (rotamer-1) | IR (cm$^{-1}$): 3411, 1612, 1574, 1462, 1136, 1070, 686; $^1$H-NMR (CDCl$_3$): 8.11 (d, J = 2.3 Hz, 1H), 7.99 (d, J = 1.6 Hz, 1H), 7.30 (dd, J = 1.6, 2.3 Hz, 1H), 3.78-3.70 (m, 1H), 3.12-3.0 (m, 4H), 2.78-2.60 (m, 6H), 2.50-2.40 (m, 1H), 2.20-2.10 (m, 1H), 2.10-2.0 (m, 1H), 1.80-1.70 (m, 1H), 1.05-0.97 (m, 1H), 0.28-0.21 (m, 1H); Mass (m/z): 337, 339 [M + H$^+$]. | |
| 9. 2-(5-Bromopyridin-3-yl)-3-(piperazin-1-ylmethyl)-2-azabicyclo[3.1.0]hexane (rotamer-2) | $^1$H-NMR (CDCl$_3$): 8.19 (d, J = 2.3 Hz, 1H), 7.98 (d, J = 1.6 Hz, 1H), 7.26 (dd, J = 1.6, 2.3 Hz, 1H), 4.88-4.80 (m, 1H), 3.80-3.70 (m, 1H), 2.95 (dd, J = 1.9, 12.1 Hz, 1H), 2.80 (dd, J = 10.2, 12.1 Hz, 1H), 2.70-2.50 (m, 7H), 2.25-2.10 (m, 2H), 2.0-1.90 (m, 1H), 1.58-1.49 (m, 1H), 1.0-0.92 (m, 1H), 0.18-0.13 (m, 1H); Mass (m/z): 337, 339 [M + H$^+$]. | |
| 10. N-[2-(Pyridin-3-yl)-2-azabicyclo[3.1.0]hex-3-ylmethyl]dimethylamine | $^1$H-NMR (CDCl$_3$): 8.30 (s, 1H), 7.96 (s, 1H), 7.12 (s, 2H), 3.70 (d, J = 12.2 Hz, 1H), 2.76 (dd, J = 9.8, 12.2 Hz, 1H), 2.70-2.60 (m, 1H), 2.33 (s, 6H), 2.20-2.05 (m, 2H), 1.95-1.86 (m, 1H), 1.52-1.43 (m, 1H), 1.0-0.93 (m, 1H), 0.20-0.12 (m, 1H); Mass (m/z): 218 [M + H$^+$]. | |
| 11. N-[2-(5-Bromopyridin-3-yl)-2-azabicyclo[3.1.0]hex-3-ylmethyl]methylamine (1:1 mix of two rotamers) | IR (cm$^{-1}$): 3303, 2933, 2795, 1572, 1455, 1366, 1235, 1104, 996, 839, 696; $^1$H-NMR (CDCl$_3$): 8.21 (d, J = 2.5 Hz, 0.5H), 8.14 (d, J = 2.5 Hz, 0.5H), 8.03-7.97 (m, 1H), 7.30-7.27 (m, 1H), 3.82-3.75 (m, 0.5H), 3.58-3.52 (m, 0.5H), 3.10-3.02 (m, 0.5H), 2.83-2.73 (m, 1H), 2.70-2.60 (m, 1H), 2.60-2.54 (m, 0.5H), 2.48 (s, 3H), 2.48-2.38 (m, 0.5H), 2.28-2.20 (m, 0.5H), 2.15-2.05 (m, 0.5H), 1.82-1.73 (m, 1H), 1.08-0.98 (m, 1H), 0.30-0.15 (m, 1H); Mass (m/z): 282, 284 [M + H$^+$]. | |
| 12. N-[2-(5-Chloropyridin-3-yl)-2-azabicyclo[3.1.0]hex-3-yl methyl]methylamine fumarate (2:3 mix of rotamers) | IR (cm$^{-1}$): 3584, 3066, 2930, 2794, 1574, 1463, 1424, 1373, 1236, 1109, 1001, 841, 697; $^1$H-NMR (CD$_3$OD): 8.22 (d, J = 2.5 Hz, 0.4H), 8.13 (d, J = 2.5 Hz, 0.6H), 7.92 (d, J = 2.0 Hz, 0.6H), 7.90 (d, J = 2.0 Hz, 0.4H), 7.40-7.45 (m, 0.4H), 7.39-7.37 (m, 0.6H), 6.69 (s, 2H), 4.17-4.10 (m, 0.6H), 3.82-3.75 (m, 0.4H), 3.32-3.10 (m, 2.6H), 2.80-2.70 (m, 0.4H), 2.75 (s, 3H), 2.28-2.20 (m, 2H), 1.95-1.85 (m, 0.6H), 1.61-1.52 (m, 0.4H), 1.18-1.13 (m, 1H), 0.48-0.35 (m, 1H); Mass (m/z): 238, 240 [M + H$^+$]. | |
| 13. [2-(5-Chloropyridin-3-yl)-2-azabicyclo[3.1.0]hex-3-yl]methylamine fumarate | IR (cm$^{-1}$): 3361, 3066, 2936, 1575, 1464, 1426, 1375, 1338, 1240, 1203, 1110, 1002, 843, 770; $^1$H-NMR (CD$_3$OD): 8.12 (d, J = 2.5 Hz, 1H), 7.92 (d, J = 2.0 Hz, 1H), 7.37 (t, J = 2.0 Hz, 1H), 6.69 (s, 2H), 4.12-4.05 (m, 1H), 3.25-3.10 (m, 3H), 2.30-2.17 (m, 2H), 1.95-1.86 (m, 1H), 1.12-1.05 (m, 1H), 0.37-0.33 (m, 1H); Mass (m/z): 224, 226 [M + H$^+$]. | |
| 14. N-[2-(5-Methoxypyridin-3-yl)-2-azabicyclo[3.1.0]hex-3-yl methyl]methylamine fumarate (~2:3 mix of rotamers) | IR (cm$^{-1}$): 3421, 1630, 1581, 1482, 1462, 1410, 1383, 1239, 1189, 980, 810, 677, 653; $^1$H-NMR (CD$_3$OD): 7.91 (d, J- 2.2 Hz, 0.6H), 7.81 (d, J = 2.2 Hz, 0.4H), 7.70 (d, J = 2.2 Hz, 0.4H), 7.68 (d, J = 2.2 Hz, 0.6H), 6.94 (dd, J = 2.2, 4.2 Hz, 0.6H), 6.88 (dd, J = 2.2, 4.4 Hz, 0.4H), 6.69 (s, 2H), 4.15-4.08 (m, 0.4H), 3.72 (dd, J = 3.4, 12.4 Hz, 0.6H), 3.40-3.20 (m, 2H), 3.18-3.10 (m, 0.6H), 2.85-2.75 (m, 0.4H), 2.79 (d, J = 5.3 Hz, 3H), 2.30-2.15 (m, 2H), 1.95-1.87 (m, 0.4H), 1.60-1.50 (m, 0.6H), 1.18-1.02 (m, 1H), 0.37-0.27 (m, 1H); Mass (m/z): 234 [M + H$^+$]. | |
| 15. N-[2-(5-Isopropoxypyridin-3-yl)-2-azabicyclo[3.1.0]hex-3- | IR (cm$^{-1}$): 3584, 2975, 2930, 2795, 1585, 1474, 1439, 1373, 1249, 1206, 1112, 1030, 831; $^1$H-NMR (CDCl$_3$): 7.94 (d, J = 2.3 Hz, 0.7H), 7.87 (d, J = 2.3 Hz, 0.3H), 7.72-7.68 (m, 1H), 6.70-6.65 (m, 1H), 4.65-4.52 (m, | |

| | | |
|---|---|---|
| | ylmethyl]methylamine (~7:3 mix of rotamers) | 1H), 3.80-3.70 (m, 0.3H), 3.57 (dd, J = 3.3, 12.0 Hz, 0.7H), 3.12-3.05 (m, 0.3H), 2.85-2.72 (m, 0.7H), 2.70-2.58 (m, 1H), 2.48 (s, 3H), 2.48-2.40 (m, 0.7H), 2.25-2.05 (m, 1.3H), 1.80-1.70 (m, 1H), 1.45-1.38 (m, 1H), 1.37-1.34 (m, 6H), 0.92-0.82 (m, 1H), 0.28-0.18 (m, 1H); Mass (m/z): 262 [M + H$^+$]. |
| 16. | [2-(5-Phenylsulfanylpyridin-3-yl)-2-azabicyclo[3.1.0]hex-3-yl]methylamine fumarate (~2:3 mix of rotamers) | IR (cm$^{-1}$): 3433, 3053, 2943, 1637, 1572, 1451, 1372, 1287, 1250, 1175, 979, 748; $^1$H-NMR (CD$_3$OD): 8.12 (d, J = 2.6 Hz, 0.4H), 8.04 (d, J = 2.6 Hz, 0.6H), 7.78 (s, 1H), 7.45-7.35 (m, 5H), 7.30-7.25 (m, 1H), 6.69 (s, 2H), 4.08-4.0 (m, 0.6H), 3.73-3.68 (m, 0.4H), 3.30-3.10 (m, 2H), 3.08-3.0 (m, 0.6H), 2.75-2.68 (m, 0.4H), 2.30-2.05 (m, 2H), 1.90-1.82 (m, 0.6H), 1.61-1.51 (m, 0.4H), 1.07-0.98 (m, 1H), 0.33-0.22 (m, 1H); Mass (m/z): 298 [M + H$^+$]. |
| 17. | N-[2-(5-phenylsulfanylpyridin-3-yl)-2-azabicyclo[3.1.0]hex-3-yl methyl]methylamine fumarate (~1:1 mix of rotamers) | IR (cm$^{-1}$): 3584, 3472, 3330, 3064, 2929, 2794, 1574, 1462, 1425, 1372, 1236, 1200, 1109, 1001, 841, 696; $^1$H-NMR (DMSO-D$_6$): 8.20 (d, J = 2.2 Hz, 0.5H), 8.11 (d, J = 2.2 Hz, 0.5H), 7.77 (s, 1H), 7.42-7.28 (m, 5H), 7.17-7.10 (m, 1H), 6.47 (s, 2H), 4.10-3.98 (m, 0.5H), 3.83-3.75 (m, 0.5H), 3.70-3.62 (m, 0.5H), 3.20-3.10 (m, 0.5H), 2.87-2.70 (m, 1H), 2.69-2.60 (m, 1H), 2.51 (s, 3H), 2.20-2.12 (m, 0.5H), 2.10-2.0 (m, 1H), 1.80-1.68 (m, 1H), 1.47-1.38 (m, 0.5H), 0.90-0.80 (m, 1H), 0.20-0.13 (m, 0.5H), 0.10-0.03 (m, 0.5H); Mass (m/z): 312 [M + H$^+$]. |
| 18. | [2-(Pyridin-3-yl)-2-azabicyclo[3.1.0]hex-3-yl] methylamine fumarate (~1:1 mix of rotamers) | IR (cm$^{-1}$): 3433, 3073, 2929, 1567, 1492, 1375, 1285, 1256, 1179, 981, 797, 704, 645; $^1$H-NMR (CD$_3$OD): 8.25 (d, J = 2.0 Hz, 0.5H), 8.20 (d, J = 2.0 Hz, 0.5H), 7.96 (d, J = 2.5 Hz, 0.5H), 7.93 (d, J = 2.5 Hz, 0.5H), 7.45-7.25 (m, 2H), 6.69 (s, 2H) 4.07-4.0 (m, 0.5H), 3.75-3.65 (m, 0.5H), 3.22-3.10 (m, 2H), 3.09-3.01 (m, 0.5H), 2.80-2.72 (m, 0.5H), 2.35-2.05 (m, 2H), 1.92-1.85 (m, 0.5H), 1.60-1.50 (m, 0.5H), 1.20-1.11 (m, 0.5H), 1.10-1.0 (m, 0.5H), 0.32-0.23 (m, 1H); Mass (m/z): 190 [M + H$^+$]. |
| 19. | [2-(3-Bromo-2-ethoxypyridin-5-yl)-2-azabicyclo[3.1.0]hex-3-yl-methyl]methylamine fumarate (~1:1 mix of rotamers) | IR (cm$^{-1}$): 3584, 3018, 2959, 2930, 1638, 1579, 1216, 1093, 755, 666; $^1$H-NMR (CD$_3$OD): 7.53 (d, J = 2.4 Hz, 0.5H), 7.39 (d, J = 2.4 Hz, 0.5H), 7.25 (d, J = 2.4 Hz, 0.5H), 7.18 (d, J = 2.4 Hz, 0.5H), 6.70 (s, 2H) 4.10-3.97 (m, 2.5H), 3.90-3.82 (m, 0.5H), 3.20-3.08 (m, 2H), 3.07-3.01 (m, 0.5H), 2.88 (s, 1.5H), 2.85-2.75 (m, 0.5H), 2.74 (s, 1.5H), 2.48-2.38 (m, 0.5H), 2.18-2.10 (m, 0.5H), 2.0-1.80 (m, 1H), 1.32 (t, J = 7.1 Hz, 3H), 1.30-1.20 (m, 1H), 1.17-1.10 (m, 0.5H), 0.97-0.90 (m, 0.5H), 0.65-0.58 (m, 0.5H), 0.57-0.50 (m, 0.5H); Mass (m/z): 326, 328 [M + H$^+$]. |
| 20. | N-[2-(3-Hydroxy pyrazin-2-yl)-2-azabicyclo[3.1.0]hex-3-yl methyl] methylamine | IR (cm$^{-1}$): 3299, 2938, 1637, 1569, 1408, 1213, 1171, 1021, 874, 758, 650, 520; $^1$H-NMR (CDCl$_3$): 6.85 (d, J = 4.6 Hz, 1H), 6.54 (d, J = 4.6 Hz, 1H), 6.11 (bs, 1H) 4.10 (dd, J = 4.4, 12.8 Hz, 1H), 3.57 (dd, J = 7.9, 12.8 Hz, 1H), 3.48-3.38 (m, 1H), 3.0 (d, J = 5.1 Hz, 3H), 2.82-2.73 (m, 1H), 2.05 (dd, J = 6.9, 12.2 Hz, 1H), 1.72-1.55 (m, 1H), 1.48-1.40 (m, 1H), 0.57-0.50 (m, 1H), 0.40-0.30 (m, 1H); Mass (m/z): 221 [M + H$^+$]. |
| 21. | N-(2-(pyrimidin-5-yl)-2-azabicyclo[3.1.0]hex-3-ylmethyl)methyl amine fumarate (1:2 mix of rotamers) | IR (cm$^{-1}$): 3419, 2938, 2800, 1570, 1485, 1439, 1377, 1197, 1086, 864; $^1$H-NMR (DMSO-d$_6$): 8.51 (s, 0.7H), 8.48 (s, 0.3H), 8.42 (s, 1H), 8.36 (s, 1H), 6.47 (s, 2H), 3.92-3.85 (m, 0.7H), 3.82-3.75 (m, 0.3H), 3.40-3.30 (m, 1H), 3.0-2.80 (m, 1.4H), 3.76-3.70 (m, 0.6H), 2.46 (s, 2.1H), 2.43 (s, 0.9H), 2.26-2.01 (m, 2H), 1.85-1.72 (m, 0.7H), 1.52-1.42 (m, 0.3H), 1.0-0.85 (m, 1H), 0.22-0.15 (m, 0.7H), 0.13-0.07 (m, 0.3H); Mass (m/z): 205 [M + H$^+$]. |
| 22. | N-(2-(pyrimidin-5-yl)-2-azabicyclo[3.1.0]hex-3-ylmethyl) amine fumarate (4:1 mixture of rotamers) | IR (cm$^{-1}$): 3385, 2938, 1574, 1486, 1444, 1378, 1334, 1205, 1085, 955, 861; $^1$H-NMR (DMSO-d$_6$): 8.52 (s, 0.8H), 8.48 (s, 0.2H), 8.39 (s, 0.8H), 8.37 (s, 1.2H), 6.43 (s, 2H), 3.95-3.85 (m, 0.8H), 3.80-3.72 (m, 0.2H), 3.32-3.20 (m, 1H), 2.96-2.70 (m, 2H), 2.25-2.0 (m, 2H), 1.85-1.70 (m, 0.8H), 1.55-1.47 (m, 0.2H), 1.0-0.85 (m, 1H), 0.22-0.10 (m, 1H); Mass (m/z): 191 [M + H$^+$]. |
| 23. | N-(2-(2-trifluoromethyl pyridin-5-yl)-2-azabicyclo[3.1.0]hex-3-ylmethyl) methyl amine fumarate (2:1 mixture of rotamers) | IR (cm$^{-1}$): 3353, 2944, 2801, 1586, 1379, 1350, 1266, 1173, 1127, 1089, 826, 757; $^1$H-NMR (CD$_3$OD): 8.39 (d, J = 2.8 Hz, 0.3H), 8.29 (d, J = 2.8 Hz, 0.7H), 7.64 (d, J = 8.7 Hz, 0.3H), 7.62 (d, J = 8.7 Hz, 0.7H), 7.47 (dd, J = 8.7, 2.8 Hz, 0.3H), 7.38 (dd, J = 8.7, 2.8 Hz, 0.7H), 6.69 (s, 2H), 4.28-4.22 (m, 0.7H), 3.92-3.85 (m, 0.3H), 3.40-3.32 (m, 0.7H), 3.35-3.12 (m, 2H), 2.87-2.80 (m, 0.3H), 2.76 (s, 3H), 2.30-2.15 (m, 2H), 2.0-1.88 (m, 0.7H), 1.65-1.58 (m, |

| | |
|---|---|
| | 0.3H), 1.22-1.12 (m, 1H), 0.40-0.26 (m, 1H);<br>Mass (m/z): 272 [M + H$^+$]. |
| 24. N-(2-(2-trifluoromethyl pyridin-5-yl)-2-azabicyclo[3.1.0]hex-3-ylmethyl) amine fumarate | IR (cm$^{-1}$): 3375, 2941, 1585, 1502, 1380, 1351, 1265, 1122, 1087, 826;<br>$^1$H-NMR (CD$_3$OD): 8.28 (d, J = 2.6 Hz, 1H), 7.62 (d, J = 8.7 Hz, 1H), 7.38 (dd, J = 8.7, 2.6 Hz, 1H), 6.69 (s, 2H), 4.22-4.15 (m, 1H), 3.40-3.30 (m, 1H), 3.18 (ddd, J = 19.2, 13.1, 6 Hz, 2H), 3.28-2.20 (m, 2H), 1.96-1.86 (m, 1H), 1.15-1.08 (m, 1H), 0.40-0.33 (m, 1H);<br>Mass (m/z): 258 [M + H$^+$]. |
| 25. N-(2-(2-chloro pyridin-5-yl)-2-azabicyclo[3.1.0]hex-3-ylmethyl) amine fumarate (2:3 mixture of rotamers) | $^1$H-NMR (CD$_3$OD): 8.02 (d, J = 2.5 Hz, 0.4H), 7.97 (d, J = 2.5 Hz, 0.6H), 7.42 (dd, J = 8.9, 2.5 Hz, 0.4H), 7.37 (dd, J = 8.9, 2.5 Hz, 0.6H), 7.29 (d, J = 8.9 Hz, 0.4H), 7.27 (d, J = 8.9 Hz, 0.6H), 6.70 (s, 2H), 4.08-4.0 (m, 0.6H), 3.72-3.65 (m, 0.4H), 3.30-3.25 (m, 0.6H), 3.25-3.0 (m, 2H), 2.80-2.72 (m, 0.4H), 2.33-2.02 (m, 2H), 1.90-1.80 (m, 0.6H), 1.60-1.50 (m, 0.4H), 1.16-1.08 (m, 0.4H), 1.10-1.0 (m, 0.6H), 0.35-0.25 (m, 1H);<br>Mass (m/z): 224, 226 [M + H$^+$]. |
| 26. N-(2-(3-methyl pyridin-5-yl)-2-azabicyclo[3.1.0]hex-3-ylmethyl) amine fumarate (1:1 mixture of rotamers) | $^1$H-NMR (CD$_3$OD): 8.10 (d, J = 2.4 Hz, 0.5H), 8.02 (d, J = 2.4 Hz, 0.5H), 7.83 (s, 1H), 7.43 (d, J = 2.4 Hz, 0.5H), 7.33 (d, J = 2.4 Hz, 0.5H), 6.66 (s, 2H), 4.15-4.05 (m, 0.5H), 3.35-3.30 (m, 0.5H), 3.26-3.10 (m, 2H), 2.82-2.74 (m, 0.5H), 2.37 (s, 1.5H), 2.35 (s, 1.5H), 2.30-2.15 (m, 2.5H), 1.95-1.85 (m, 0.5H), 1.62-1.52 (m, 0.5H), 1.20-1.12 (m, 0.5H), 1.10-1.02 (m, 0.5H), 0.30-0.22 (m, 1H);<br>Mass (m/z): 204 [M + H$^+$]. |
| 27. N-(2-(3-methyl pyridin-5-yl)-2-azabicyclo[3.1.0]hex-3-ylmethyl)methyl amine bistartarate (1:2 mixture of rotamers) | $^1$H-NMR (CD$_3$OD): 8.11 (s, 0.7H), 8.04 (s, 0.3H), 7.83 (s, 0.3H), 7.81 (s, 0.7H), 7.31 (s, 0.7H), 7.24 (s, 0.3H), 4.45 (s, 2H), 4.15-4.05 (m, 0.3H), 3.80-3.72 (m, 0.7H), 3.20-3.10 (m, 1H), 2.90-2.55 (m, 2H), 2.78 (s, 2.1H), 2.76 (s, 0.9H), 2.34 (s, 3H), 2.30-2.20 (m, 2H), 1.90-1.82 (m, 0.3H), 1.60-1.50 (m, 0.7H), 1.18-1.10 (m, 0.7H), 1.10-1.02 (m, 0.3H), 0.35-0.25 (m, 1H);<br>Mass (m/z): 218 [M + H$^+$]. |
| 28. N-(2-(3-trifluoromethyl pyridin-5-yl)-2-azabicyclo[3.1.0]hex-3-ylmethyl) amine fumarate | IR (cm$^{-1}$): 3416, 2927, 1627, 1596, 1485, 1384, 1125, 1088, 956, 862;<br>$^1$H-NMR (CD$_3$OD): 8.42 (s, 1H), 8.22 (s, 1H), 7.50 (s, 1H), 6.68 (s, 2H), 4.20-4.10 (m, 1H), 3.40-3.30 (m, 1H), 3.20 (ddd, J = 22.4, 13.2, 6.2 Hz, 2H), 2.30-2.20 (m, 2H), 1.98-1.90 (m, 1H), 1.20-1.10 (m, 1H), 0.40-0.30 (m, 1H);<br>Mass (m/z): 258 [M + H$^+$]. |
| 29. N-(2-(quinolin-3-yl)-2-azabicyclo[3.1.0]hex-3-ylmethyl) amine fumarate (1:1 mixture of rotamers) | IR (cm$^{-1}$): 3423, 2928, 1594, 1486, 1459, 1386, 1254, 1084, 955, 861;<br>$^1$H-NMR (CD$_3$OD): 8.84 (d, J = 2.8 Hz, 0.5H), 8.78 (d, J = 2.8 Hz, 0.5H), 7.95-7.85 (m, 1H), 7.83-7.75 (m, 1H), 7.60 (d, J = 2.8 Hz, 0.5H), 7.57 (d, J = 2.8 Hz, 0.5H), 7.55-7.45 (m, 2H), 6.69 (s, 2H), 4.20-4.10 (m, 0.5H), 3.92-3.85 (m, 0.5H), 3.57-3.51 (m, 0.5H), 3.30-3.10 (m, 2H), 2.98-2.92 (m, 0.5H), 2.40-2.10 (m, 2H), 1.93-1.86 (m, 0.5H), 1.65-1.55 (m, 0.5H), 1.25-1.15 (m, 0.5H), 1.10-1.02 (m, 0.5H), 0.42-0.35 (m, 1H);<br>Mass (m/z): 240 [M + H$^+$]. |
| 30. N-(2-(3-trifluoromethyl pyridin-5-yl)-2-azabicyclo[3.1.0]hex-3-ylmethyl) methylamine fumarate (1:2 mixture of rotamers) | IR (cm$^{-1}$): 3417, 2930, 1627, 1597, 1484, 1382, 1142, 1126, 1089, 955, 861;<br>$^1$H-NMR (CD$_3$OD): 8.54 (s, 0.3H), 8.43 (s, 0.7H), 8.22 (s, 0.7H), 8.21 (s, 0.3H), 7.57 (s, 0.3H), 7.52 (s, 0.7H), 6.68 (s, 2H), 4.28-4.16 (m, 0.7H), 3.90-3.80 (m, 0.3H), 3.40-3.15 (m, 2.7H), 2.88-2.80 (m, 0.3H), 2.76 (s, 3H), 2.30-2.15 (m, 2H), 1.98-1.91 (m, 0.7H), 1.68-1.58 (m, 0.3H), 1.20-1.10 (m, 1H), 0.40-0.25 (m, 1H);<br>Mass (m/z): 272 [M + H$^+$]. |
| 31. N-(2-(quinolin-3-yl)-2-azabicyclo[3.1.0]hex-3-ylmethyl) methylamine fumarate (1:2 mixture of rotamers) | IR (cm$^{-1}$): 3407, 2937, 2854, 1597, 1473, 1432, 1394, 1308, 1142, 1015, 952;<br>$^1$H-NMR (CD$_3$OD): 8.87 (d, J = 2.5 Hz, 0.7H), 8.79 (d, J = 2.5 Hz, 0.3H), 7.95-7.86 (m, 1H), 7.84-7.75 (m, 1H), 7.63 (d, J = 2.5 Hz, 0.7H), 7.58 (d, J = 2.5 Hz, 0.3H), 7.55-7.45 (m, 2H), 6.69 (s, 2H), 4.30-4.22 (m, 0.3H), 3.95-3.85 (m, 0.7H), 3.58-3.52 (m, 0.3H), 3.35-3.20 (m, 2H), 2.98-2.92 (m, 0.7H), 2.79 (s, 2.1H), 2.77 (s, 0.9H), 2.40-2.20 (m, 2H), 1.95-1.88 (m, 0.3H), 1.68-1.55 (m, 0.7H), 1.25-1.15 (m, 0.7H), 1.12-1.03 (m, 0.3H), 0.45-0.35 (m, 1H);<br>Mass (m/z): 254 [M + H$^+$]. |
| 32. Benzofuran-2-yl-(3-methylaminomethyl-2-azabicyclo[3.1.0]hex-2-yl)methanone tartrate | $^1$H-NMR (CD$_3$OD): 7.85-7.73 (m, 2H), 7.61 (d, J = 8.3 Hz, 1H), 7.50 (t, J = 7.5 Hz, 1H), 7.35 (t, J = 7.5 Hz, 1H), 4.45 (s, 2H), 3.91-3.82 (m, 1H), 3.50-3.10 (m, 3H), 2.75 (s, 3H), 2.25-2.15 (m, 1H), 2.10-2.0 (m, 2H), 1.38-1.29 (m, 1H), 0.85-0.79 (m, 1H);<br>Mass (m/z): 271 [M + H$^+$]. |
| 33. (7-Bromo benzofuran-2-yl)-(3-methylaminomethyl-2-azabicyclo[3.1.0]hex-2- | $^1$H-NMR (CD$_3$OD): 7.82 (s, 1H), 7.77 (d, J = 7.8 Hz, 1H), 7.67 (d, J = 7.6 Hz, 1H), 7.28 (t, J = 7.8 Hz, 1H), 4.48 (s, 2H), 3.98-3.90 (m, 1H), 3.50-3.45 (m, 1H), 3.44-3.20 (m, 2H), 2.76 (s, 3H), 2.28-2.20 (m, 1H), 2.15-2.05 (m, 2H), 1.40-1.30 (m, 1H), |

| | -continued | |
|---|---|---|
| | yl) methanone tartrate | 0.85-0.78 (m, 1H);<br>Mass (m/z): 349, 351 [M + H⁺]. |
| 34. | (3-Aminomethyl-2-azabicyclo[3.1.0]hex-2-yl)-(1H-indol-2-yl)-methanone | IR (cm⁻¹): 3267, 2929, 1597, 1526, 1440, 1343, 1325, 809, 744;<br>¹H-NMR (CDCl₃): 9.30 (bs, 1H), 7.69 (d, J = 8.0 Hz, 1H), 7.45 (d, J = 8.1 Hz, 1H), 7.33-7.22 (m, 2H), 7.15 (t, J = 7.5 Hz, 1H), 4.58-4.48 (m, 1H), 3.60-3.50 (m, 1H), 3.10-3.0 (m, 1H), 3.0-2.90 (m, 1H), 2.18-2.10 (m, 1H), 2.10-1.91 (m, 2H), 1.38-1.30 (m, 1H), 0.77-0.70 (m, 1H);<br>Mass (m/z): 256 [M + H⁺]. |
| 35. | (3-Aminomethyl-2-azabicyclo[3.1.0]hex-2-yl) furan-2-yl methanone tartrate | IR (cm⁻¹): 3423, 2935, 2875, 1618, 1600, 1480, 1420, 1197, 1077, 1030, 954, 861, 759;<br>¹H-NMR (CD₃OD): 7.77 (s, 1H), 7.40 (d, J = 3.2 Hz, 1H), 6.64 (d, J = 3.2 Hz, 1H), 4.68-4.58 (m, 1H), 4.40 (s, 2H), 3.78-3.70 (m, 1H), 3.35-3.18 (m, 2H), 2.16 (dd, J = 12.8, 8.6 Hz, 1H), 2.10-1.93 (m, 2H), 1.25-1.18 (m, 1H), 0.72-0.63 (m, 1H);<br>Mass (m/z): 207 [M + H⁺]. |
| 36. | (3-Aminomethyl-2-azabicyclo[3.1.0]hex-2-yl) (5-bromo pyridin-3-yl) methanone tartrate | IR (cm⁻¹): 3385, 2926, 1628, 1486, 1458, 1412, 1199, 1021, 954, 743, 699;<br>¹H-NMR (CD₃OD): 8.86 (s, 1H), 8.79 (d, J = 2.0 Hz, 1H), 8.35 (d, J = 2.0 Hz, 1H), 4.60-4.52 (m, 1H), 4.42 (s, 2H), 3.38-3.30 (m, 1H), 3.30-3.18 (m, 2H), 2.26 (dd, J = 13.6, 8.3 Hz, 1H), 2.15-2.08 (m, 1H), 1.98-1.88 (m, 1H), 1.0-0.92 (m, 1H), 0.80-0.75 (m, 1H);<br>Mass (m/z): 296, 298[M + H⁺]. |
| 37. | (3-Aminomethyl-2-azabicyclo[3.1.0]hex-2-yl) pyridin-2-yl methanone tartrate (3:2 mix of isomers) | ¹H-NMR (CD₃OD): 8.64 (bs, 1H), 8.18-8.10 (m, 0.6H), 8.08-7.90 (m, 1H), 7.80-7.72 (m, 0.4H), 7.62-7.52 (m, 1H), 4.68-4.58 (m, 1H), 4.42 (s, 2H), 3.68-3.40 (m, 3H), 2.32-2.20 (m, 1H), 2.15-2.0 (m, 1H), 1.90-1.80 (m, 1H), 1.02-0.95 (m, 0.6H), 0.93-0.75 (m, 1H), 0.60-0.53 (m, 0.4H);<br>Mass (m/z): 218 [M + H⁺]. |
| 38. | (3-Aminomethyl-2-azabicyclo[3.1.0]hex-2-yl) pyridin-3-yl methanone tartarate (3:2 mix of isomers) | IR (cm⁻¹): 3422, 2926, 1625, 1591, 1485, 1389, 1198, 1077, 1028, 956, 861, 767, 742, 708;<br>¹H-NMR (CD₃OD): 9.02 (s, 0.4H), 8.90 (s, 0.6H), 8.75-8.65 (m, 1H), 8.30 (d, J = 7.3 Hz, 0.4H), 8.20 (d, J = 7.4 Hz, 0.6H), 7.60-7.52 (m, 1H), 4.62-4.52 (m, 1H), 4.42 (s, 2H), 3.80-3.75 (m, 0.6H), 3.70-3.60 (m, 0.4H), 3.30-3.10 (m, 2H), 2.35-2.22 (m, 1H), 2.18-2.0 (m, 1H), 1.98-1.80 (m, 1H), 1.05-0.92 (m, 1H), 0.90-0.75 (m, 1H);<br>Mass (m/z): 218 [M + H⁺]. |
| 39. | (3-Aminomethyl-2-azabicyclo[3.1.0]hex-2-yl) pyridin-4-yl methanone tartarate (1:1 mix of isomers) | IR (cm⁻¹): 3420, 2925, 1627, 1592, 1486, 1386, 1300, 1254, 1199, 1076, 955, 861, 767, 742, 700;<br>¹H-NMR (DMSO-d₆): 8.73 (d, J = 5.4 Hz, 1H), 8.70 (d, J = 5.1 Hz, 1H), 7.74 (d, J = 5.4 Hz, 1H), 7.61 (d, J = 5.1 Hz, 1H), 4.50-4.40 (m, 1H), 4.0 (s, 2H), 3.20-3.0 (m, 3H), 2.10-2.0 (m, 1H), 1.80-1.70 (m, 1.5H), 1.60-1.52 (m, 0.5H), 0.90-0.75 (m, 1H), 0.70-0.64 (m, 0.5H), 0.60-0.50 (m, 0.5H);<br>Mass (m/z): 218 [M + H⁺]. |

Examples 40-67

The person skilled in the art can prepare the compounds of Examples 40-67 by following the procedures described above.

40. N-[2-(pyridin-3-yl)-2-azabicyclo[3.1.0]hex-3-ylmethyl)methylamine;
41. 5-(3-Methylaminomethyl-2-azabicyclo[3.1.0]hex-2-yl)nicotinonitrile;
42. N-[2-(2,3-Dichloropyridin-5-yl)-2-azabicyclo[3.1.0]hex-3-ylmethyl]methylamine;
43. N-[2-(5-Isopropoxypyridin-3-yl)-2-azabicyclo[3.1.0]hex-3-ylmethyl]methylamine;
44 N-[2-(5-methylpyridin-3-yl)-2-azabicyclo[3.1.0]hex-3-ylmethyl]methylamine;
45. l-[5-(3-Methylaminomethyl-2-azabicyclo[3.1.0]hex-2-yl)pyridin-3-yl]pyrrolidin-2-one;
46. 5-(3-Methylaminomethyl-2-azabicyclo[3.1.0]hex-2-yl)nicotinamide;
47. N-[2-(5-Bromopyridin-3-yl)-2-azabicyclo[3.1.0]hex-3-ylmethyl]methylamine;
48. N-[2-(5-Methoxypyridin-3-yl)-2-azabicyclo[3.1.0]hex-3-ylmethyl]methylamine;
49. [5-(3-methylaminomethyl-2-azabicyclo[3.1.0]hex-2-yl)pyridin-3-yl]methylamine;
50. 2-(5-Bromopyridin-3-yl)-3-(pyrrolidin-1-ylmethyl)-2-azabicyclo[3.1.0]hexane;
51. [2-(5-Bromopyridin-3-yl)-2-azabicyclo[3.1.0]hex-3-yl]methylamine;
52. N-[2-(pyridin-3-yl)-2-azabicyclo[3.1.0]hex-3-ylmethyl)dimethylamine;
53. 5-(3-Dimethylaminomethyl-2-azabicyclo[3.1.0]hex-2-yl)nicotinonitrile;
54. N-[2-(2,3-Dichloropyridin-5-yl)-2-azabicyclo[3.1.0]hex-3-ylmethyl]dimethylamine;
55. N-[2-(5-Isopropoxypyridin-3-yl)-2-azabicyclo[3.1.0]hex-3-ylmethyl]dimethylamine;
56. N-[2-(5-methylpyridin-3-yl)-2-azabicyclo[3.1.0]hex-3-ylmethyl]dimethylamine;
57. 1-[5-(3-Dimethylaminomethyl-2-azabicyclo[3.1.0]hex-2-yl)pyridin-3-yl]pyrrolidin-2-one;
58. 5-(3-Dimethylaminomethyl-2-azabicyclo[3.1.0]hex-2-yl)nicotinamide;
59. N-[2-(5-Bromopyridin-3-yl)-2-azabicyclo[3.1.0]hex-3-ylmethyl]dimethylamine;
60. N-[2-(5-Methoxypyridin-3-yl)-2-azabicyclo[3.1.0]hex-3-ylmethyl]dimethylamine;
61. [5-(3-Dimethylaminomethyl-2-azabicyclo[3.1.0]hex-2-yl)pyridin-3-yl]methylamine;
62. (3-Aminomethyl-2-azabicyclo[3.1.0]hex-2-yl)-benzofuran-2-yl-methanone;

-continued 63. (3-Aminomethyl-2-azabicyclo[3.1.0]hex-2-yl)-(7-bromobenzofuran-2-yl) methanone;
64. (4-Chloro furan-2-yl) (3-methylaminomethyl-2-azabicyclo[3.1.0]hex-2-yl) methanone;
65. (3-Aminomethyl-2-azabicyclo[3.1.0]hex-2-yl)-(4-bromo furan-2-ylmethanone;
66. (3-Aminomethyl-2-azabicyclo[3.1.0]hex-2-yl)-(4-chloro-furan-2-yl) methanone;
67. (4-Chlorofuran-2-yl)-(3-methylaminomethyl-2-azabicyclo[3.1.0]hex-2-yl) methanone;

Biological Assays

Example 68

Binding Assay for Human or Rat Nicotinic Acetylcholine $\alpha_4\beta_2$ Receptor Compounds can be evaluated according to the following procedures.
Materials and Methods:
  Receptor source: Rat brain frontal cortex or recombinant human cDNA expressed in CHO cells
  Radioligand: [$^3$H]Cytisine 15-40 Ci/mmole
  Final ligand concentration—[2.5 nM]
  Non-specific determinant: Epibatidine—[0.1 µM]
  Reference compound: Epibatidine
  Positive control: Epibatidine
Incubation Conditions:
  Increasing concentrations of test compounds or standard were incubated with membrane receptors and radioligand in 120 mM NaCl, 2.5 mM KCl, 1 mM CaCl$_2$, 1 mM MgCl$_2$ and 50 mM TRIS-HCl (pH 7.4) for 60 minutes at room temperature. The reaction was terminated by rapid vacuum filtration onto the glass fiber filters. Radioactivity trapped onto the filters was determined and compared to the control values in order to ascertain any interactions of the test compound(s) with either cloned human or rat receptor binding site.

| Example Number | $K_i$ (nM) |
|---|---|
| 1. | 23 |
| 2. | 7 |
| 3. | 41.7 |
| 4. | 59.4 |
| 5. | 700 |
| 8. | 610 |
| 10. | 77 |
| 11. | 46.4 |
| 12. | 77.3 |
| 13. | 3.5 |
| 14. | 179 |
| 15. | 383 |
| 16. | 451 |
| 18. | 6.4 |
| 20. | 13.0 |
| 21. | 465 |
| 22. | 58.13 |
| 23. | 2 |
| 24. | 681 |
| 25. | 6.9 |
| 26. | 5.7 |
| 27. | 253 |
| 28. | 140 |
| 29. | 135 |
| 30. | 247 |
| 31. | 1646 |
| 32. | 38.3 |

| Example Number | $K_i$ (nM) |
|---|---|
| 33. | 2997 |
| 34. | 55.0 |
| 35. | 38.7 |
| 36. | 17.8 |
| 37. | 11.6 |
| 38. | 45 |
| 39. | 109 |

Literature Reference: Bunnelle W. H., Daanen J. F., Ryther K. B., Schrimpf M. R., Dart M. J., Gelain A., Meyer M. D., Frost J. M., Anderson D. J., Buckley M., Curzon P., Cao Y-J., Puttfarcken P., Searle X., Ji J., Putman C. B., Surowy C., Toma L. and Barlocco D. Structure-Activity Studies and Analgesic Efficacy of N-(3-Pyridinyl)-Bridged Bicyclic Diamines, Exceptionally Potent Agonists at Nicotinic Acetylcholine Receptors. J. Med. Chem. 2007, 50, 36-27.

Example 69

Determination of IC$_{50}$ and K$_b$ Values for Nicotinic Acetylcholine $\alpha_4\beta_2$ Receptor Ligands A stable CHO cell line expressing recombinant human $\alpha_4\beta_2$ nicotinic acetylcholine receptor transiently expressing aequorin protein was used for cell-based assay. The assay offers a non-radioactive based approach to determine binding of a compound to ligand gated ion channels. In this specific assay, the level of intracellular calcium, which is modulated by activation or inhibition of the channel is measured. Both the channel and aequorin genes are expressed at high level under the control of powerful CMV promotor.

The above cells were grown in 96 well clear bottom white plates in Hams F12 medium containing 10% fetal bovine serum (FBS). Prior to the addition of compounds and/or agonist, cells were serum starved for six hours. Coelentarazine (a prosthetic group for aequorin protein) was added in the medium containing 0.1% dialyzed serum and incubated overnight at 27° C. Cells were washed with assay buffer and increasing concentration of the test compound or standard were added to the plate for antagonist mode. A fixed concentration of the agonist (eipbatidine) was injected into the plate and luminescence was measured for 10 seconds. For evaluation of the compound in agonist mode, increasing concentration of the standard or test compound were injected and the luminescence was measured. Luminescence units were plotted against the compound concentrations using Graphpad software. IC$_{50}$ values of the compounds were defined as the concentration required in reducing the luminescent units by 50%. The K$_b$ values were calculated by feeding the concentration of the agonist used in the assay and its EC$_{50}$ value in the same software.

| Example Number | $K_b$ (nM) |
|---|---|
| 1. | 1.4 |
| 8. | 4.6 |
| 9. | 73.1 |
| 10. | 3.4 |

Literature References: Karadsheh M. S., Shah M. S., Tang X., Macdonald R. L. and Stitzel J. A. Functional characterization of mouse $\alpha_4\beta_2$ nicotinic acetylcholine receptors stably expressed in HEK293T cells. J. Neurochem. 2004, 91, 1138-1150.

Example 70

Rodent Pharmacokinetic Study

Male wistar rats (230-280 grams) obtained from NIN (National Institute of Nutrition, Hyderabad, India) were used as an experimental animal. Three to five animals were housed in each cage. Animals were kept fasted over night and maintained on a 12 hours light/dark cycle. Three rats were dosed NCE orally (15 or 5 mg/kg) and intravenously (5 mg/kg) on day 0 and day 2

At each time point blood was collected by jugular vein. Plasma was stored frozen at −20° C. until analysis. The concentrations of the NCE compound in plasma were determined using LC-MS/MS method. Schedule time points: Pre dose 0.25, 0.5, 1, 1.5, 2, 3, 4, 6, 8, 10, 12 and 24 hours after dosing (n=3). The NCE compounds were quantified in plasma by validated LC-MS/MS method using solid phase extraction technique. NCE compounds were quantified in the calibration range of 1-2000 ng/mL in plasma. Study samples were analyzed using calibration samples in the batch and quality control samples spread across the batch.

Pharmacokinetic parameters $C_{max}$, $T_{max}$, $AUC_t$, $T_{1/2}$ and Bioavailability were calculated by non-compartmental model using software WinNonlin version 5.0.1.

Example 71

Rodent Brain Penetration Study

Male Wister rats (230-280 grams) obtained from NIN (National Institute of Nutrition, Hyderabad, India) was used as an experimental animal. Three animals were housed in each cage. Animals were given water and food ad libitum throughout the experiment, and maintained on a 12 hours light/dark cycle.

NCE compound was dissolved in water and administered orally. At $T_{max}$ (0.5, 1.0 and 2.0) animals were sacrificed to collect the plasma and brain tissue and were homogenized. Plasma and Brain was stored frozen at −20° C. until analysis. The concentrations of the NCE compound in plasma and Brain were determined using LC-MS/MS method.

The NCE compounds were quantified in plasma and brain homogenate by validated LC-MS/MS method using solid phase extraction technique. NCE compounds were quantified in the calibration range of 1-500 ng/mL in plasma and brain homogenate. Study samples were analyzed using calibration samples in the batch and quality control samples spread across the batch. Extents of brain-blood ratio were calculated ($C_b/C_p$).

| Example Number | Strain/ Gender | Dose (mg/kg) | Vehicle | Route of administration | $C_{max}$ (ng/mL) | $T_{max}$ (h) | $AUC_t$ (ng.hr/mL) | $T_{1/2}$ (h) | Bioavailability (%) |
|---|---|---|---|---|---|---|---|---|---|
| 1. | Wister rat/Male | 15 | Water for injection | Per-Oral | 219 ± 120 | 0.25 ± 0.00 | 273 ± 160 | 0.58 ± 0.13 | 10 ± 5 |
|  | Wister rat/Male | 5 | Water for injection | Intravenous | 1935 ± 260 | 0.14 ± 0.10 | 901 ± 47 | 0.99 ± 0.25 |  |
| 4. | Wister rat/Male | 15 | Water for injection | Per-Oral | 1559 ± 294 | 0.33 ± 0.14 | 5275 ± 652 | 4.48 ± 0.76 | 105 ± 9 |
|  | Wister rat/Male | 5 | Water for injection | Intravenous | 956 ± 164 | 0.08 ± 0.00 | 1670 ± 154 | 5.82 ± 0.53 |  |
| 11. | Wister rat/Male | 15 | Water for injection | Per-Oral | 1993 ± 435 | 0.31 ± 0.13 | 3875 ± 846 | 1.92 ± 1.20 | 59 ± 31 |
|  | Wister rat/Male | 5 | Water for injection | Intravenous | 1438 ± 330 | 0.08 ± 0.00 | 2538 ± 1301 | 1.45 ± 0.53 |  |
| 13. | Wister rat/Male | 5 | Water for injection | Per-Oral | 753 ± 277 | 0.38 ± 0.14 | 1536 ± 165 | 1.75 ± 0.40 | 89 ± 18 |
|  | Wister rat/Male | 5 | Water for injection | Intravenous | 836 ± 239 | 0.08 ± 0.00 | 1755 ± 228 | 1.43 ± 0.11 |  |
| 18. | Wister rat/Male | 5 | Water for injection | Per-Oral | 355 ± 53 | 0.08 ± 0.00 | 1536 ± 165 | 1.75 ± 0.40 | 87 ± 24 |
|  | Wister rat/Male | 5 | Water for injection | Intravenous | 701 ± 213 | 0.38 ± 0.14 | 1755 ± 228 | 1.43 ± 0.11 |  |
| 21. | Wister rat/Male | 5 | Water for injection | Per-Oral | 685 ± 107 | 0.63 ± 0.25 | 1971 ± 100 | 1.30 ± 0.37 | 101 ± 20 |
|  | Wister rat/Male | 5 | Water for injection | Intravenous | 1570 ± 261 | 0.08 ± 0.00 | 2026 ± 525 | 1.43 ± 0.18 |  |
| 22. | Wister rat/Male | 5 | Water for injection | Per-Oral | 1104 ± 211 | 0.08 ± 0.00 | 2018 ± 377 | 1.63 ± 0.11 | 89 ± 9 |
|  | Wister rat/Male | 5 | Water for injection | Intravenous | 1376 ± 156 | 0.25 ± 0.00 | 2247 ± 228 | 1.34 ± 0.07 |  |
| 23. | Wister rat/Male | 5 | Water for injection | Per-Oral | 2310 ± 163 | 0.33 ± 0.14 | 12000 ± 1744 | 5.12 ± 0.19 | 67 ± 9 |
|  | Wister rat/Male | 5 | Water for injection | Intravenous | 3641 ± 89 | 0.08 ± 0.00 | 18007 ± 3296 | 6.92 ± 2.42 |  |
| 35. | Wister rat/Male | 5 | Water for injection | Per-Oral | 998 ± 175 | 0.33 ± 0.14 | 1312 ± 146 | 1.49 ± 0.26 | 92 ± 8 |
|  | Wister rat/Male | 5 | Water for injection | Intravenous | 1780 ± 56 | 0.08 ± 0.00 | 1422 ± 71 | 1.13 ± 0.15 |  |

| Example Number | Strain/ Gender | Dose (mg/kg) | Vehicle | Route of administration | Brain Penetration Index ($C_b/C_p$) |
|---|---|---|---|---|---|
| 4. | Wister rat/Male | 15 | Water for injection | Per-Oral | 11.74 ± 2.66 |
|  | Wister rat/Male | 5 | Water for injection | Intravenous |  |
| 11. | Wister rat/Male | 15 | Water for injection | Per-Oral | 8.75 ± 1.589 |
|  | Wister rat/Male | 5 | Water for injection | Intravenous |  |
| 13. | Wister rat/Male | 5 | Water for injection | Per-Oral | 10.84 ± 1.29 |
|  | Wister rat/Male | 5 | Water for injection | Intravenous |  |
| 18. | Wister rat/Male | 5 | Water for injection | Per-Oral | 3.52 ± 0.13 |
|  | Wister rat/Male | 5 | Water for injection | Intravenous |  |
| 21. | Wister rat/Male | 5 | Water for injection | Per-Oral | 1.74 ± 0.27 |
|  | Wister rat/Male | 5 | Water for injection | Intravenous |  |
| 23. | Wister rat/Male | 5 | Water for injection | Per-Oral | 1.97 ± 0.08 |
|  | Wister rat/Male | 5 | Water for injection | Intravenous |  |

Example 72

Object Recognition Task Model

The cognition-enhancing properties of compounds of this invention were estimated using a model of animal cognition: the object recognition task model.

Male Wister rats (230-280 grams) obtained from N. I. N. (National Institute of Nutrition, Hyderabad, India) was used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

Some representative compounds have shown positive effects indicating the increased novel object recognition viz; increased exploration time with novel object and higher discrimination index.

| Example Number | Dose mg/kg, p.o. | Exploration time mean ± S.E.M (sec) Familiar object | Novel object | Inference |
|---|---|---|---|---|
| 4. | 1 mg/kg | 7.64 ± 1.052 | 14.21 ± 2.364 | Active |
| 12. | 1 mg/kg | 4.651 ± 0.619 | 16.70 ± 2.136 | Active |
| 13. | 0.1 mg/kg | 7.32 ± 1.04 | 22.77 ± 2.12 | Active |
| 35. | 0.3 mg/kg | 5.30 ± 1.05 | 14.90 ± 7.74 | Active |

Example 73

Water Maze

Water maze consisted of a 1.8 m diameter; 0.6 m high circular water maze tub filled with water. A platform was placed 1.0 cm below the water surface in the center of one of the four imaginary quadrants, which remained constant for all the rats. Rats were administered with vehicle or test compound before acquisition training and half hour after administration of vehicle or test compound; scopolamine was administered. Rats were lowered gently, feet first into water. A rat was allowed to swim for 60 seconds to find the platform. If the platform was found during this time the trial was stopped and rat was allowed to stay on platform for 30 seconds before being removed from the maze. If the platform was not found during 60 seconds trials, then the rat was manually placed on the platform. Each rat received 4 trials in a day. Retention of the task was assessed on 5th day in which each animal received a single 120 seconds probe trial in which platform removed from the pool. Time spent in target quadrant (ms) (quadrant in which platform is placed during acquisition training was calculated for probe trial. Latency to reach the platform (ms), swim speed (cm/s) and path length (cm) was measured in acquisition trials.

Example 74

Mouse Forced Swim Assay

The animals were administered with vehicle or test drug prior to testing. Then the animals were individually placed inside the plexiglass cylinder containing water for 6 minutes. The initial 2 minutes will be not be scored and remaining 4 minutes was observed for immobility behavior. Immobility behavior is defined as no movement of animal except little action to keep the head above the water level. The water was changed after every trial.

Example 75

DRL-72s

The antidepressant properties of compounds of this invention were evaluated using a model of animal depression: the DRL-72s model. Male Sprague Dawley rats were used as experimental animals. Rats are trained to lever press for a 4" access to 0.025 ml of water for each correct response during daily 60 minute sessions. All testing takes place on weekdays only. At the beginning of each session, the house light is illuminated and remains lit until the session ends. No other stimuli are presented during testing. After successful lever press training, rats are then required to respond under a DRL-24 second schedule, where only lever presses that are separated by 24 seconds are reinforced. Upon stable responding on a DRL-24 second schedule (5-10 sessions), rats are trained on a DRL-72 second schedule until responding stabilizes at approximately 15% efficiency (approx 25-35 sessions). Specifically, rats receive a reinforcer for each response that is emitted at least 72 seconds after the previous response (IRT). Responses with IRT's less than 72 seconds do not receive a reinforcer, and the IRT requirement is reset to 72 seconds. Efficiency is recorded as number of reinforced responses÷total number of responses. After stable baseline responding is achieved, defined as responding for 4 consecutive sessions with no more than 10% variability, animals begin drug testing. Animals receive drug no more than 1× per week.

| Example Number | Dose |
|---|---|
| 4. | ≥10 mg/kg, p.o. |
| 13. | ≥10 mg/kg, p.o. |

Example 76

Reversal of Formalin Induced Nociception

The anti-nociceptive properties of compounds of this invention were evaluated using a model of pain: the Formalin Induced Nociception model. Male Wister rats (230-280 grams) obtained from N. I. N. (National Institute of Nutrition, Hyderabad, India) was used as experimental animals.
Rats were habituated for 20 minutes in the arena before the experiment was started. Duration of licks, bites and flinches were noted from 0-10 minutes and 20-35 minutes after administration of formalin, subplantar into the right hind paw at concentrations of 5% v/v. 50 μL of water for injection was injected into the right hind paw of the rats of the sham group. Compounds of this invention were administered orally prior to formalin administration.

| Example Number | Dose |
|---|---|
| 4. | ≤10 mg/kg, p.o. |
| 13. | ≥30 mg/kg, p.o. |

Example 77

Acute Food Intake Study

The appetite suppressing properties of compounds of this invention were studied using an animal model of hyperphagia.
Male Wister rats (200-210 grams) obtained from Raj Biotech, India were used as experimental animals. The experiment consisted of 6 days. The rats were adapted to the 18 hour fasting and 6 hour feeding pattern. The animals were housed in a group of three in the cages provided with the fasting grills and were fasted for 18 hours. After 18 hour fasting the rats were separated and placed individually in a cage. Weighed amount of feed was provided to rats for 6 hour and the feed intake at 1, 2, 4 and 6 hours was recorded. Again the rats were regrouped and fasted for 18 hour. The above procedure was followed for 5 days. The average cumulative food intake by the rats on the last 3 days was calculated. Animals were randomised on the basis of their last three days food intake.

One group of 8 rats received vehicle (2 mL/Kg) orally and another set of animals received compound of the formula (I) orally. Then the rats were given access to food and the food intake at 1, 2, 4 and 6 hours was recorded. The food intake by the rats treated with test compound was compared with the vehicle treated group by using students 't' test.

Some representative compounds have shown positive effects indicating the suppression of food intake i.e. hypophagia like effects.

| Example Number | % Suppression of food intake compared to vehicle | | | | Inference |
|---|---|---|---|---|---|
| | 1 Hour | 2 Hour | 4 Hour | 6 Hour | |
| 4. | 38.45% | 30.23% | 25.60% | 18.63% | Active |
| 18. | 36.80% | 33.05% | 30.02% | 25.38% | Active |

Example 78

Effect of Test Compounds on Body Weight Gain in High Fat Fed Rats

The body weight gain suppressing properties of compounds of this invention were studied using a animal model of obesity.

Male Sprague Dawley rats (150-160 grams) obtained from Reliance Life Sciences, India were used as experimental animals. Rats were fed with control diet (normal pellet diet) and lard based high fat diet (45% kcal diet) for 7-8 weeks. High fat diet fed animals was randomized according to their body weights. The animals were housed in a group of 3-4 per cage. One group of 10 rats received vehicle (2 mL/Kg) orally and another set of animals received compound of the formula (I) orally for 14 days. Body weight of the animals was recorded for first three consecutive days then it was recorded twice weekly. Weighed amount of food was given to the animals and food intake was recorded every 24 hour for the entire study period.

Some representative compounds have shown positive effects indicating the decrease in the body weight gain.

| Example Number | % Reduction in body weight gain compared to vehicle (Day 14) | Inference |
|---|---|---|
| 4. | 3.3% | Active |

We claim:
1. A compound of the general formula (I):

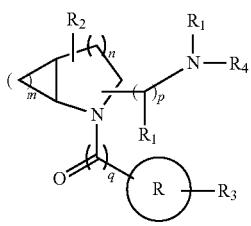

wherein,

represents pyridinyl, furyl, pyrazinyl, pyrimidinyl, quinolinyl, benzofuranyl or indolyl;
$R_1$ represents hydrogen or methyl;
$R_2$ represents hydrogen;
$R_3$ represents hydrogen, hydroxy, bromo, chloro, methyl, methoxy, ethoxy, isopropoxy or trifluoromethyl;
$R_4$ represents hydrogen, methyl or ethyl; optionally $R_1$ and $R_4$ along with nitrogen atom may form pyrrolidine, morpholine or piperazine;
"m" represents 1;
"n" represents 1;
"p" represents 0 to 2;
"q" represents 0 to 1; or their stereoisomers & pharmaceutically acceptable salts.

2. The compound according to claim 1, which is selected from the group consisting of:
N-[2-(5-Bromopyridin-3-yl)-2-azabicyclo[3.1.0]hex-3-ylmethyl]-dimethylamine hydrochloride;
[2-(5-Bromopyridin-3-yl)-2-azabicyclo-[3.1.0]-hex-3-yl]methylamine;
Furan-2-yl-(3-methylaminomethyl-2-aza bicyclo[3.1.0]hex-2-yl)methanone tartarate;
N-[2-(Pyridin-3-yl)-2-azabicyclo[3.1.0]hex-3-ylmethyl] methylamine hydrochloride;
N-[2-(5-Bromopyridin-3-yl)-2-azabicyclo[3.1.0]hex-3-ylmethyl]ethylamine tartarate;
2-(5-Bromopyridin-3-yl)-3-pyrrolidin-1-ylmethyl-2-azabicyclo[3.1.0]hexane tartarate;
2-(5-Bromopyridin-3-yl)-3-(morpholin-4-ylmethyl)-2-azabicyclo[3.1.0]hexane tartarate;
2-(5-Bromopyridin-3-yl)-3-(piperazin-1-ylmethyl)-2-azabicyclo[3.1.0]hexane;
N-[2-(Pyridin-3-yl)-2-azabicyclo[3.1.0]hex-3-ylmethyl] dimethylamine;
N-[2-(5-Bromopyridin-3-yl)-2-azabicyclo[3.1.0]hex-3-ylmethyl]methylamine;
N-[2-(5-Chloropyridin-3-yl)-2-azabicyclo[3.1.0]hex-3-yl methyl]methylamine fumarate;
[2-(5-Chloropyridin-3-yl)-2-aza-bicyclo[3.1.0]hex-3-yl] methylamine fumarate;
N-[2-(5-Methoxypyridin-3-yl)-2-azabicyclo[3.1.0]hex-3-yl methyl]methylamine fumarate;
N-[2-(5-Isopropoxypyridin-3-yl)-2-azabicyclo[3.1.0]hex-3-ylmethyl]methylamine;
[2-(Pyridin-3-yl)-2-azabicyclo[3.1.0]hex-3-yl]methylamine fumarate;
[2-(3-Bromo-2-ethoxypyridin-5-yl)-2-azabicyclo[3.1.0] hex-3-yl-methyl]methylamine fumarate;
N-[2-(3-Hydroxy pyrazin-2-yl)-2-azabicyclo[3.1.0]hex-3-yl methyl]methylamine;
N-(2-(pyrimidin-5-yl)-2-azabicyclo[3.1.0]hex-3-ylmethyl)methyl amine fumarate;
N-(2-(2-trifluoromethylpyridin-5-yl)-2-azabicyclo[3.1.0] hex-3-ylmethyl)methyl amine fumarate;
N-(2-(2-trifluoromethylpyridin-5-yl)-2-azabicyclo[3.1.0] hex-3-ylmethyl)amine fumarate;
N-(2-(2-chloro pyridin-5-yl)-2-azabicyclo[3.1.0]hex-3-ylmethyl)amine fumarate;
N-(2-(3-methylpyridin-5-yl)-2-azabicyclo[3.1.0]hex-3-ylmethyl)amine fumarate;
N-(2-(3-methylpyridin-5-yl)-2-azabicyclo[3.1.0]hex-3-ylmethyl)methyl amine bistartarate;
N-(2-(3-trifluoromethylpyridin-5-yl)-2-azabicyclo[3.1.0] hex-3-ylmethyl)amine fumarate;
N-(2-(quinolin-3-yl)-2-azabicyclo[3.1.0]hex-3-ylmethyl) amine fumarate;
N-(2-(3-trifluoromethylpyridin-5-yl)-2-azabicyclo[3.1.0] hex-3-ylmethyl)methylamine fumarate;
N-(2-(quinolin-3-yl)-2-azabicyclo[3.1.0]hex-3-ylmethyl) methylamine fumarate;
Benzofuran-2-yl-(3-methylaminomethyl-2-azabicyclo [3.1.0]hex-2-yl)methanone tartrate;
(7-Bromo benzofuran-2-yl)-(3-methylaminomethyl-2-azabicyclo[3.1.0]hex-2-yl) methanone tartrate;
(3-Aminomethyl-2-azabicyclo[3.1.0]hex-2-yl)-(1H-indol-2-yl)-methanone;
(3-Aminomethyl-2-aza bicyclo[3.1.0]hex-2-yl)furan-2-yl methanone tartrate;
(3-Aminomethyl-2-azabicyclo[3.1.0]hex-2-yl)(5-bromo pyridin-3-yl)methanone tartrate;
(3-Aminomethyl-2-azabicyclo[3.1.0]hex-2-yl)pyridin-2-yl methanone tartrate;
(3-Aminomethyl-2-aza bicyclo[3.1.0]hex-2-yl)pyridin-3-yl methanone tartarate; and
(3-Aminomethyl-2-aza-bicyclo[3.1.0]hex-2-yl)pyridin-4-yl methanone tartarate; or their stereoisomers and pharmaceutically acceptable salts.

3. A process for the preparation of a compound of formula (I) as claimed in claim 1, which comprises:
(a) coupling the compound of formula (12) with compound of formula (13)

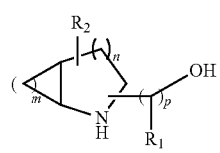

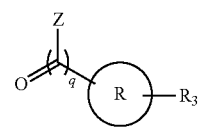

to form a compound of formula (14);

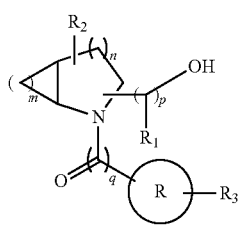
(14)

(b) converting the hydroxyl group of formula (14) to mesylate group of formula (15);

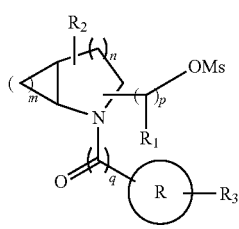
(15)

(c) reacting the compound of formula (15) with alkylamines to form compound of formula (I), wherein all substitutions are as defined in claim 1 and "Z" represents halogen;
(d) optionally converting the compound of formula (I) to their stereoisomers or pharmaceutically acceptable salts.

4. A process for the preparation of a compound of formula (I) as claimed in claim 1, which comprises:
(a) coupling the compound of formula (12) with compound of formula (13)

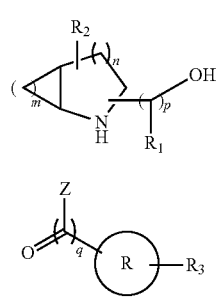
(12)

(13)

to form a compound of formula (14);

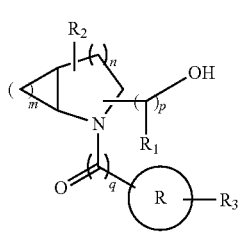
(14)

(b) converting the hydroxyl group of formula (14) to mesylate group of formula (15);

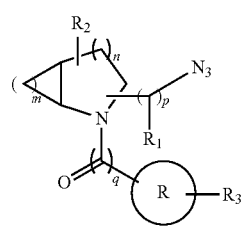
(15)

(c) reacting the compound of formula (15) with azide to form compound of formula (16);

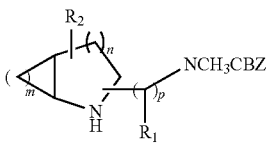
(16)

(d) reducing the compound of formula (16) to form compound of formula (I), wherein all substitutions are as defined in claim 1 and "Z" represents halogen;
(e) optionally converting the compound of formula (I) to their stereoisomers or pharmaceutically acceptable salts.

5. A process for the preparation of a compound of formula (I) as claimed in claim 1, which comprises:
(a) coupling the compound of formula (17) with compound of formula (13)

(17)

(13)

to form a compound of formula (19);

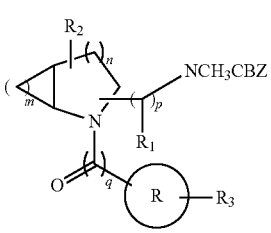
(19)

(b) deprotecting the compound of formula (19) to form compound of formula (I), wherein all substitutions are as defined in claim 1 and "Z" represents halogen;

(c) optionally converting the compound of formula (I) to their stereoisomers or pharmaceutically acceptable salts.

6. A pharmaceutical composition comprising a compound according to any of claims 1 to 2 and pharmaceutically acceptable excipient.

7. The pharmaceutical composition according to claim 6, for the treatment of one or more clinical conditions selected from the group consisting of anxiety, Alzheimer's disease, depression, attention deficit hyperactivity disorder, pain, Parkinson's disease, schizophrenia, and obesity, in a patient having said one or more conditions.

8. A method for the treatment of a disorder of the central nervous system related to or affected by the $\alpha_4\beta_2$ nicotinic receptor, in a patient having said disorder, which comprises the step of providing to said patient a therapeutically effective amount of a compound of formula (I) as defined in any one of claims 1 to 2.

9. The method according to claim 8, wherein the said disorder is anxiety, Alzheimer's disease, depression, attention deficit hyperactivity disorder, pain, Parkinson's disease, schizophrenia, or obesity.

\* \* \* \* \*